United States Patent
Borrebaeck et al.

(10) Patent No.: US 9,863,960 B2
(45) Date of Patent: Jan. 9, 2018

(54) METHOD, ARRAY AND USE FOR DETERMINING THE PRESENCE OF PANCREATIC CANCER

(75) Inventors: Carl Arne Krister Borrebaeck, Lund (SE); Lars Bertil Christer Wingren, Sodra Sandby (SE)

(73) Assignee: IMMUNOVIA AB, Lund (SE)

( * ) Notice: Subject to any disclaimer, the term of this patent is extended or adjusted under 35 U.S.C. 154(b) by 300 days.

(21) Appl. No.: 14/002,494

(22) PCT Filed: Mar. 5, 2012

(86) PCT No.: PCT/GB2012/050483
§ 371 (c)(1),
(2), (4) Date: Oct. 8, 2013

(87) PCT Pub. No.: WO2012/120288
PCT Pub. Date: Sep. 13, 2012

(65) Prior Publication Data
US 2014/0038844 A1 Feb. 6, 2014

(30) Foreign Application Priority Data
Mar. 4, 2011 (GB) .................................. 1103726.4

(51) Int. Cl.
| G01N 33/566 | (2006.01) |
| G01N 33/563 | (2006.01) |
| G01N 33/544 | (2006.01) |
| C07K 16/00 | (2006.01) |
| G01N 33/68 | (2006.01) |
| G01N 33/574 | (2006.01) |

(52) U.S. Cl.
CPC ... *G01N 33/6893* (2013.01); *G01N 33/57438* (2013.01)

(58) Field of Classification Search
None
See application file for complete search history.

(56) References Cited

U.S. PATENT DOCUMENTS

2007/0212738 A1  9/2007 Haley et al.

FOREIGN PATENT DOCUMENTS

| CN | 101613748 | 12/2009 |
| CN | 101880707 | 11/2010 |
| JP | 2004-248575 | 9/2004 |
| JP | 2007-051880 | 1/2007 |
| WO | 2006/110581 | 10/2006 |
| WO | 2006/110599 | 10/2006 |
| WO | 2006/113210 | 10/2006 |
| WO | 2007/045966 | 4/2007 |
| WO | 2007/107774 | 9/2007 |
| WO | 2008/079269 | 7/2008 |
| WO | 2008/117067 | 10/2008 |
| WO | WO 2009/068857 | * 4/2009 | .......... G01N 33/574 |
| WO | 2010/102195 | 9/2010 |
| WO | 2011/010969 | 1/2011 |
| WO | 2012/120288 | 9/2012 |
| WO | 2015/067969 | 5/2015 |

OTHER PUBLICATIONS

Grizzle et al. 2010. Cancer Res. 70(8 Suppl) Abstract 2732.*
Wingren et al. 2012. 72:2481-90.*
Al-Rawi et al. 2004. Eur. J. Cancer. 40:494-502.*
Wenke et al 2007. Cellular Oncology. 29:373-386.*
Rutkowski et al. 2010. Mol. Cancer Res. 8:1453-65.*
Derin et al. 2007. Lung Cancer. 59:240-245.*
Herman et al. 2011. Blood. 117:6287-6296.*
Lambeck et al. 2007.Clin Cancer Res.13:2385-.*
Brand et al. 2011. Clin. Cancer Res. 17:805-816.*
Orchekokowski et al. 2005. Cancer Res. 65:11193-202.*
Chang, S.T., et al. "Identification of a biomarker panel using a multiplex proximity ligation assay improves accuracy of pancreatic cancer diagnosis." J Transl Med. Dec. 11, 2009;7:105.
Grzesiak, J.J., et al. "The integrin-extracellular matrix axis in pancreatic cancer." Pancreas. Nov. 2007;35(4):293-301.
Pepe, M.S., et al., "Phases of Biomarker Development for Early Detection of Cancer" J. Natl. Cancer Institute (2001) 93(14): 1054-1061.
Xie, H., et al., "Mining of Microarray, Proteomics, and Clinical Data for Improved Identification of Chronic Fatigue Syndrome" Critical Assessment of Microarray Data Analysis (CAMDA) Conference (2006) Durham, North Carolina.
Crnogorac-Jurcevic, T., et al., "Proteomic Analysis of Chronic Pancreatitis and Pancreatic Adenocarcinoma," Gastroenterology (2005)129:1454-1463.
Fujiwara, S., et al., "Transforming Activity of the Lymphotoxin-B Receptor Revealed by Expression Screening," Biochem. Biophys. Res. Comm. (2005) 338:1256-1262.
Ingvarsson, J., et al., "Detection of Pancreatic Cancer using Antibody Microarray-based Serum Protein Profiling," Proteomics (2008) 8:2211-2219.
Jiang, W.G., et al., "Angiomotin and Angiomotin Like Proteins, Their Expression and Correlation with Angiogenesis and Clinical Outcome in Human Breast Cancer," BMC Cancer (2006) 6:16.
Karayiannakis, A.G., et al., "Serum Vascular Endothelial Growth Factor Levels in Pancreatic Cancer Patients Correlate with Advanced and Metastatic Disease and Poor Prognosis," Cancer Letters (2003) 194:119-124.
Li, M., et al., "Cyclophilin A is Overexpressed in Human Pancreatic Cancer Cells and Stimulates Cell Proliferation through CD147," Cancer (2006) 106:2284-2294.
Monti, P., et al., "The CC Chemokine MCP-1/CCL2 in Pancreatic Cancer Progression: Regulation of Expression and Potential Mechanisms of Antimalignant Activity," Cancer Res. (2003) 63:7451-7461.

(Continued)

*Primary Examiner* — Shulamith H Shafer
(74) *Attorney, Agent, or Firm* — Robert C. Netter, Jr.; Dann, Dorfman, Herrell & Skillman

(57) ABSTRACT

The present invention relates to a method for determining the presence of pancreatic cancer in an individual comprising or consisting of the steps of: (a) providing a sample to be tested from the individual, and (b) determining a biomarker signature of the test sample by measuring the expression in the test sample of one or more biomarkers selected from the group defined in Table III, wherein the expression in the test sample of one or more biomarkers selected from the group defined in Table III is indicative of the individual having pancreatic cancer. The invention also comprises arrays and kits of parts for use in the method of the invention.

2 Claims, 11 Drawing Sheets

(56) References Cited

OTHER PUBLICATIONS

Figure 1A:
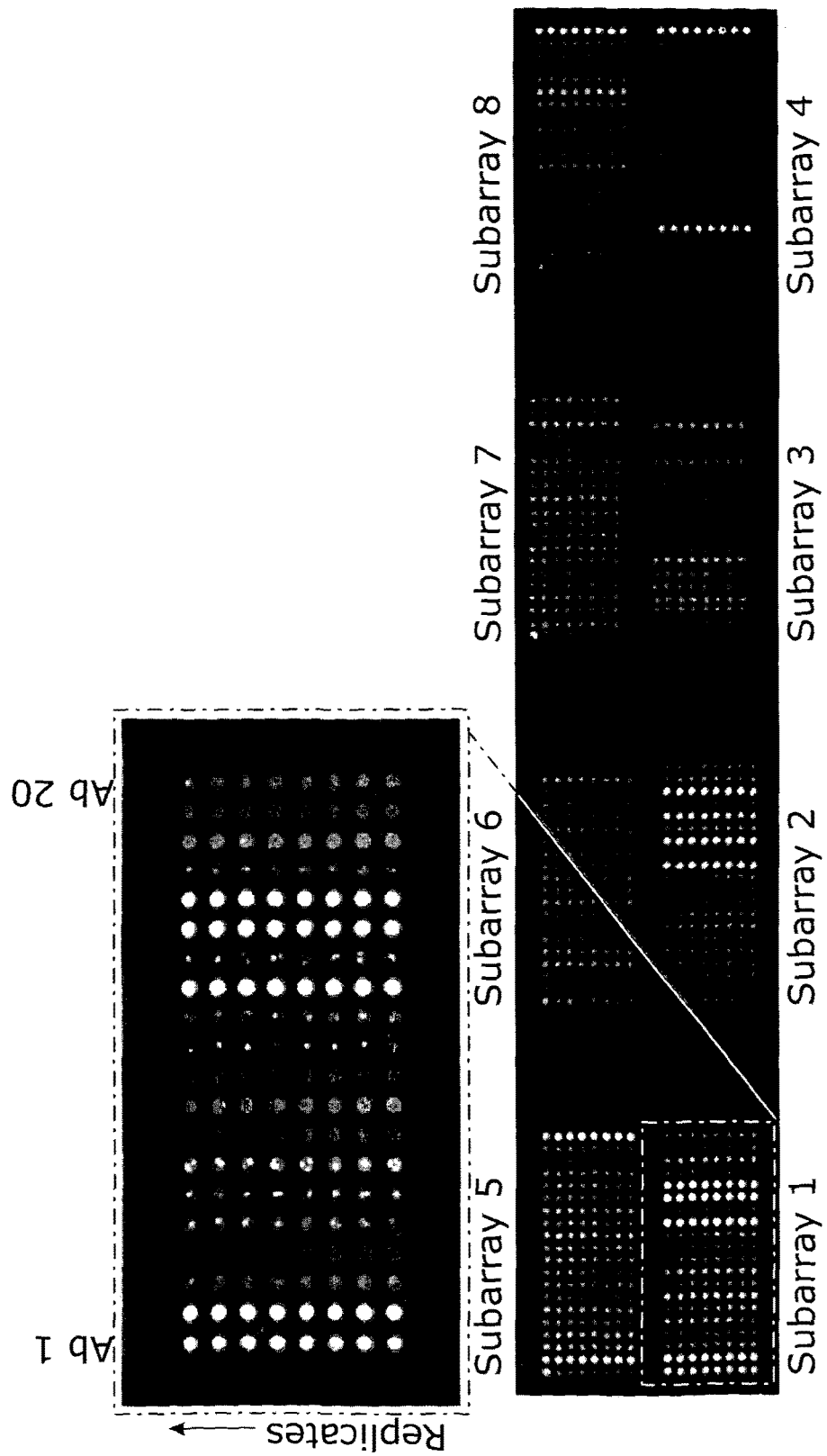

Pauly, F., et al., "Protein Expression Profiling of Formalin-Fixed Paraffin-Embedded Tissue Using Recombinant Antibody Microarrays," J. Proteome Res. (2013) 12:5943-5953.

Szajda, S.D., et al., "Carbohydrate Markers of Pancreatic Cancer," Biochem. Soc. Transactions (2011) 39:340-343.

Wingren, C., et al., "Identification of Serum Biomarker Signatures Associated with Pancreatic Cancer," Cancer Res. (2012) 72:2481-2490.

Zhang, L., et al., "Expression of c-erbB-2 Oncogene Protein, Epidermal Growth Factor Receptor, and TGF-β1 in Human Pancreatic Ductal Adenocarcinoma," Hepatobiliary Pancreat. Dis. Int. (2002) 1:620-623.

Orr, F.W., et al., "Detection of a Complement-Derived Chemotactic Factor for Tumor Cells in Human Inflammatory and Neoplastic Effusions," Am. J. Pathol. (1983) 110(1):41-7.

Geetha, A., et al., "Assessment of Immunity Status in Patients with Pancreatic Cancer" J. Clin. Biochem. Nutr. (2006) 39:18-26.

Cho, J.H., et al., "W1412: Expression of Sox-11 and Sox-4 is Involved in Pathogenesis of Solid Pseudopapillary Tumor in Pancreas," Gastroenterology (2008) 134:A-699.

Li, H., et al., "Expressions of Syk and VEGF-D Protein in Pancreatic Cancer and Their Clinical Significance" Chinese J. Cancer Prev. Treat. (2008) 15(15):1166-1168 [Abstract only].

Winikoff, S., et al., "Abstract 166—A Novel Method of Pancreatic Cancer Detection by Simultaneous Analysis of Multiple Serum Markers" Annals of Surgical Oncology (2004) 11(Suppl 2):S114.

Zhou, "Clinical Research and Empirical Study of Combination Treatment with Gemcitabine Chemotherapy and Huai'er Granula on Pancreatic Cancer" Master's Thesis Full-Text Database, Medicine and Health Sciences (2009) 5:E72-E130 [Abstract only].

\* cited by examiner

PaC vs. N
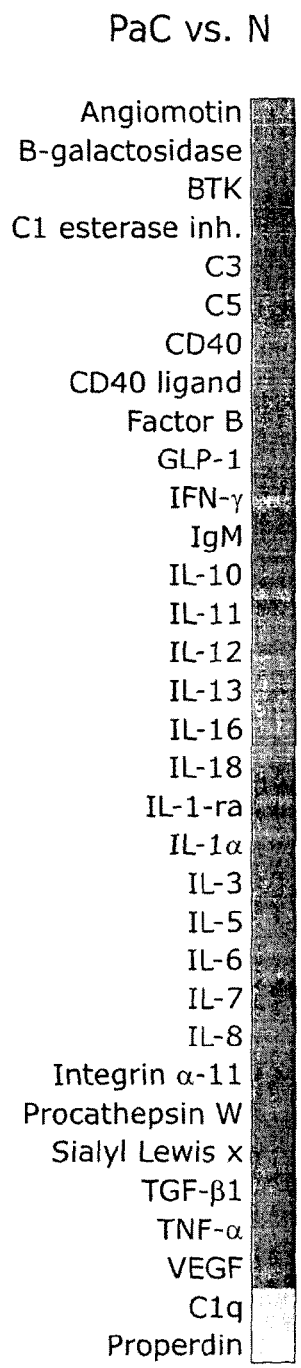
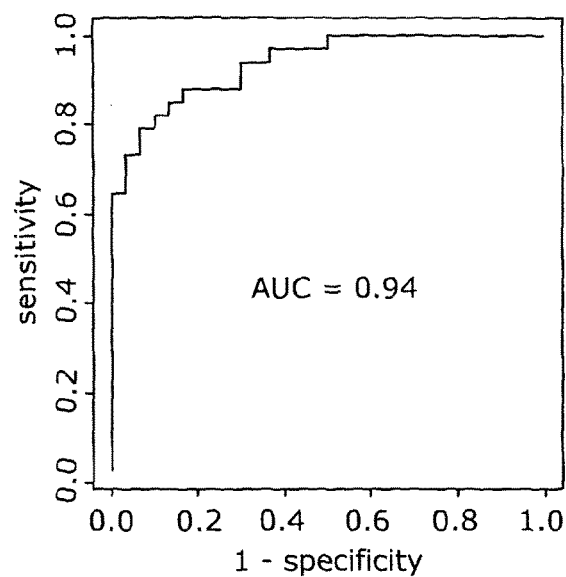
Figure 1(C)
Figure 1(B)

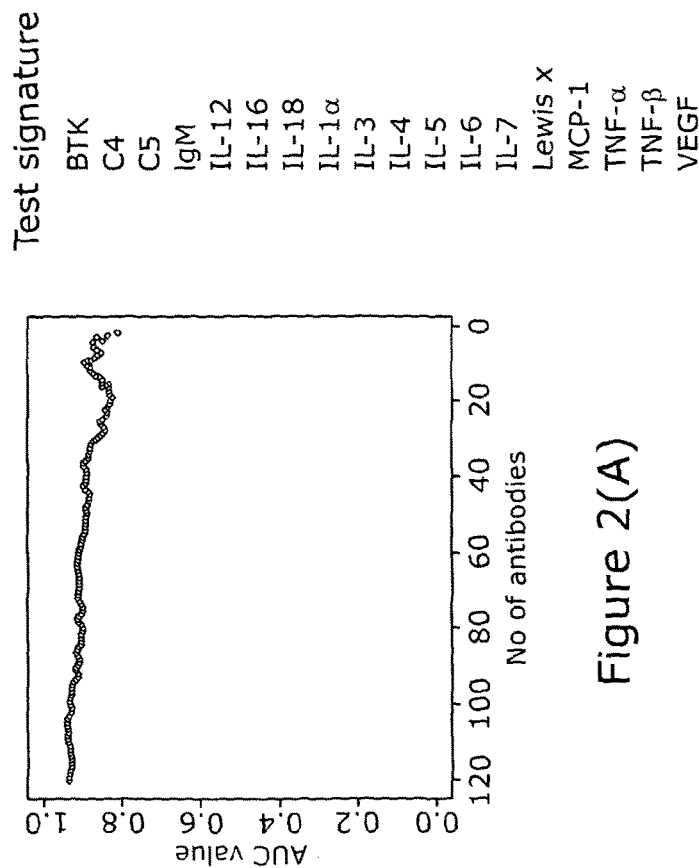
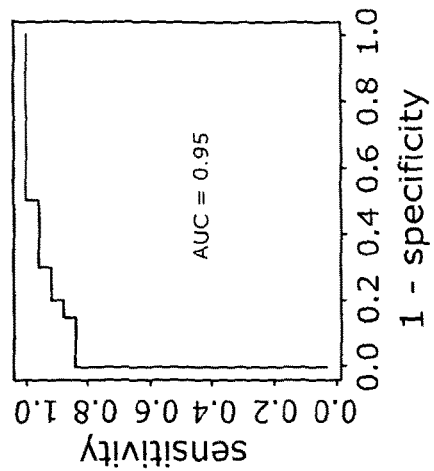
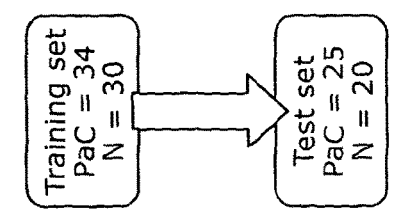
Figure 2(A)   Figure 2(B)   Figure 2(C)   Figure 2(D)
Test signature
BTK
C4
C5
IgM
IL-12
IL-16
IL-18
IL-1α
IL-3
IL-4
IL-5
IL-6
IL-7
Lewis x
MCP-1
TNF-α
TNF-β
VEGF
Training set
PaC = 34
N = 30
Test set
PaC = 25
N = 20
AUC = 0.95

SEQUENCE LISTING

<160> NUMBER OF SEQ ID NOS: 2

<210> SEQ ID NO 1
<211> LENGTH: 242
<212> TYPE: PRT
<213> ORGANISM: Homo sapiens

<400> SEQUENCE: 1

```
Met Ala Glu Val Gln Leu Leu Glu Ser Gly Gly Gly Leu Val Gln Pro
1               5                   10                  15

Gly Gly Ser Leu Arg Leu Ser Cys Ala Ala Ser Gly Phe Thr Phe Ser
            20                  25                  30

Ser Tyr Gly Phe His Trp Val Arg Gln Ala Pro Gly Lys Gly Leu Glu
        35                  40                  45

Trp Val Ser Leu Ile Ser Trp Asp Gly Gly Ser Thr Tyr Tyr Ala Asp
    50                  55                  60

Ser Val Lys Gly Arg Phe Thr Ile Ser Arg Asp Asn Ser Lys Asn Thr
65                  70                  75                  80

Leu Tyr Leu Gln Met Asn Ser Leu Arg Ala Glu Asp Thr Ala Val Tyr
                85                  90                  95

Tyr Cys Ala Arg Gly Thr Trp Phe Asp Pro Trp Gly Gln Gly Thr Leu
            100                 105                 110

Val Thr Val Ser Ser Gly Gly Gly Ser Gly Gly Gly Gly Ser Gly
        115                 120                 125

Gly Gly Gly Ser Gln Ser Val Leu Thr Gln Pro Pro Ser Ala Ser Gly
    130                 135                 140

Thr Pro Gly Gln Arg Val Thr Ile Ser Cys Ser Gly Ser Ser Ser Asn
145                 150                 155                 160

Ile Gly Asn Asn Ala Val Asn Trp Tyr Gln Gln Leu Pro Gly Thr Ala
                165                 170                 175

Pro Lys Leu Leu Ile Tyr Arg Asn Asn Gln Arg Pro Ser Gly Val Pro
            180                 185                 190

Asp Arg Phe Ser Gly Ser Lys Ser Gly Thr Ser Ala Ser Leu Ala Ile
        195                 200                 205

Ser Gly Leu Arg Ser Glu Asp Glu Ala Asp Tyr Tyr Cys Ala Ala Trp
    210                 215                 220

Asp Asp Ser Leu Ser Trp Val Phe Gly Gly Gly Thr Lys Leu Thr Val
225                 230                 235                 240

Leu Gly
```

<210> SEQ ID NO 2
<211> LENGTH: 31
<212> TYPE: PRT
<213> ORGANISM: Artificial Sequence
<220> FEATURE:
<223> OTHER INFORMATION: 6-His affinity tag -continued

```
<400> SEQUENCE: 2

Asp Tyr Lys Asp His Asp Gly Asp Tyr Lys Asp His Asp Ile Asp Tyr
1               5                   10                  15

Lys Asp Asp Asp Asp Lys Ala Ala Ala His His His His His His
            20                  25                  30
```

METHOD, ARRAY AND USE FOR DETERMINING THE PRESENCE OF PANCREATIC CANCER

This application is a §371 application of PCT/GB2012/050483, filed Mar. 5, 2012, which in turn claims priority to GB Application 1103726.4, filed Mar. 4, 2011. The entire disclosure of each of the foregoing applications is incorporated by reference herein.

FIELD OF INVENTION

The present invention relates to methods for diagnosis of pancreatic cancer, and biomarkers and arrays for use in the same.

BACKGROUND

Despite major efforts, pancreatic cancer (PaC) still carries a poor prognosis [1]. While PaC is only the $10^{th}$ most common cancer, it is the $4^{th}$ leading cause of cancer death in the USA [2-4]. In fact, the 5-year survival is <5%, the lowest of all malignancies [2-3]. However, recent data have shown that the outcome could be dramatically improved by early detection when the cancer is still predominantly at stage I, as illustrated by a 5-year survival of 30-60% (≤20 mm sized tumour) and even >75% (≤10 mm sized tumour) after early PaC resection [2-4].

PaC is characterized by a rapid tumour progression, early metastasization, and unresponsiveness to most conventional therapies [1, 5]. The poor prognosis is mainly due to the lack of effective early diagnostics combined with that disease-specific clinical symptoms occur late in the course of the disease. At the time of diagnosis, the tumour has often reached a size of 30-40 mm and a majority of all patients (52%) already have metastases, 26% locally advanced cancer, and only 7% have tumours confined to the pancreas [2, 4]. At this time, about 15% of the patients are still operable, but their median survival is only 20 months.

A variety of non-invasive methodologies, including (endoscopic) ultrasound, computed tomography, and/or endoscopic retrograde cholangio-pancreatography, are used for PaC diagnostics [1-2, 6]. Albeit powerful, these methods are not specific for PaC and not designed for early detection when the tumour is still small and potentially curable. The situation is further complicated by the fact that PaC is difficult to differentiate from benign conditions, such as chronic pancreatitis, using currently available diagnostic tools [2]. Hence, the use of biomarkers for specific and early detection of PaC would be of invaluable clinical benefit.

In spite of major efforts, molecular fingerprints associated with PaC from in particular, crude, non-fractionated serum and plasma, remains to be deciphered [2, 7-9]. Among the number of mainly single biomarkers that have been outlined so far, including e.g. CRP, CA 242, GDF-15, haptoglobin, M2-pyruvate kinase, serum amyloid A, IGFBP-1, none have proven to be clinically superior to CA 19-9 [2, 8-10]. Still, the use of CA 19-9 is significantly hampered by the fact that it has been found to i) be elevated in both non-malignant conditions (e.g. pancreatitis and acute cholangitis) and other gastro-intestinal cancers (e.g. gastric cancer and colorectal cancer), ii) lack sensitivity for early PaC, and iii) be absent in about 10% of the population [2, 8-10]. When screening for PaC, CA 19-9 has only yielded medium sensitivity (ranging from 69% to 98%) and specificity (46% to 98%) [2, 9-11].

Against this background, the inventors developed a proteomic approach to prognostic diagnosis of cancer in WO 2008/117067 whereby the first sets of serum biomarkers for detection of pancreatic cancer and for predicting survival were identified.

SUMMARY OF THE INVENTION

Motivated by a recent study, in which we indicated that affinity proteomics [12-13] could be used to pin-point candidate PaC serum biomarker signatures [14], we have further deciphered the serum proteome of PaC.

In this study, we have for the first time pre-validated multiplexed serum biomarker signatures for PaC diagnosis, demonstrating that diagnostic information could be extracted from crude blood samples, displaying high specificity and sensitivity. This provides enhanced PaC diagnosis and thereby improved prognosis, bringing significantly added clinical value, as well as shedding further light on the underlying, intricate disease biology.

Accordingly, a first aspect of the invention provides a method for determining the presence of pancreatic cancer in an individual comprising or consisting of the steps of:
 a) providing a sample to be tested from the individual;
 b) determining a biomarker signature of the test sample by measuring the expression in the test sample of one or more biomarkers selected from the group defined in Table III;
wherein the expression in the test sample of one or more biomarkers selected from the group defined in Table III is indicative of the individual having pancreatic cancer.

By "sample to be tested", "test sample" or "control sample" we include tissue, fluid proteome and/or expressome samples from an individual to be tested or a control individual, as appropriate.

By "expression" we mean the level or amount of a gene product such as mRNA or protein.

Methods of detecting and/or measuring the concentration of protein and/or nucleic acid are well known to those skilled in the art, see for example Sambrook and Russell, 2001, Cold Spring Harbor Laboratory Press.

By "biomarker" we mean a naturally-occurring biological molecule, or component or fragment thereof, the measurement of which can provide information useful in the prognosis of pancreatic cancer. For example, the biomarker may be a naturally-occurring protein or carbohydrate moiety, or an antigenic component or fragment thereof.

In one embodiment, the method comprises or consists of steps (a) and (b) and the further steps of:
 c) providing a control sample from an individual not afflicted with pancreatic cancer (i.e. a negative control);
 d) determining a biomarker signature of the control sample by measuring the expression in the control sample of the one or more biomarkers measured in step (b);
wherein the presence of pancreatic cancer is identified in the event that the expression in the test sample of the one or more biomarkers measured in step (b) is different from the expression in the control sample of the one or more biomarkers measured in step (d).

In another embodiment, the method comprises or consists of steps (a), (b), (c) and (d) and the additional steps of:
 e) providing a control sample from an individual afflicted with pancreatic cancer (i.e. a positive control);

f) determining a biomarker signature of the control sample by measuring the expression in the control sample of the one or more biomarkers measured in step (b);

wherein the presence of pancreatic cancer is identified in the event that the expression in the test sample of the one or more biomarkers measured in step (b) corresponds to the expression in the control sample of the one or more biomarkers measured in step (f).

By "corresponds to the expression in the control sample" we include that the expression of the one or more biomarkers in the sample to be tested is the same as or similar to the expression of the one or more biomarkers of the positive control sample. Preferably the expression of the one or more biomarkers in the sample to be tested is identical to the expression of the one or more biomarkers of the positive control sample.

Differential expression (up-regulation or down regulation) of biomarkers, or lack thereof, can be determined by any suitable means known to a skilled person. Differential expression is determined to a p value of a least less than 0.05 (p=<0.05), for example, at least <0.04, <0.03, <0.02, <0.01, <0.009, <0.005, <0.001, <0.0001, <0.00001 or at least <0.000001. Preferably, differential expression is determined using a support vector machine (SVM). Preferably, the SVM is an SVM as described below. Most preferably, the SVM is the SVM described in Table V(A), below.

It will be appreciated by persons skilled in the art that differential expression may relate to a single biomarker or to multiple biomarkers considered in combination (i.e. as a biomarker signature). Thus, a p value may be associated with a single biomarker or with a group of biomarkers. Indeed, proteins having a differential expression p value of greater than 0.05 when considered individually may nevertheless still be useful as biomarkers in accordance with the invention when their expression levels are considered in combination with one or more other biomarkers.

In one embodiment, step (b) comprises or consists of measuring the expression of one or more of the biomarkers listed in Table IV(A), for example, at least 2 of the biomarkers listed in Table IV(A).

As exemplified in the accompanying examples, the expression of certain proteins in a blood, serum or plasma test sample may be indicative of pancreatic cancer in an individual. For example, the relative expression of certain serum proteins in a single test sample may be indicative of the presence of pancreatic cancer in an individual.

Preferably, the individual is a human. However, the individual being tested may be any mammal, such as a domesticated mammal (preferably of agricultural or commercial significance including a horse, pig, cow, sheep, dog and cat).

Preferably, step (b) comprises or consists of measuring the expression of interleukin-7 (IL-7) and/or integrin alpha-10, for example, measuring the expression of interleukin-7, measuring the expression of integrin alpha-10, or measuring the expression of interleukin-7 and integrin alpha-10. Most preferably, step (b) comprises or consists of measuring the expression of each the biomarkers listed in Table IV(A).

In one embodiment, step (b) comprises or consists of measuring the expression of 1 or more biomarkers from the biomarkers listed in Table IV(B), for example at least 2, 3, 4, 5, 6, 7, 8, 9, 10, 11, 12, 13, 14, 15, 16, 17 or 18 of the biomarkers listed in Table IV(B). Hence, step (b) preferably comprises or consists of measuring the expression of all of the biomarkers listed in Table IV(B).

In another embodiment, step (b) comprises or consists of measuring the expression of 1 or more biomarkers from the biomarkers listed in Table IV(C), for example at least 2, 3, 4, 5, 6, 7, 8, 9, 10, 11, 12, 13, 14, 15, 16, 17, 18, 19. 20, 21, 22, 23, 24, 25, 26, 27, 28, 29, 30, 31, 32 or 33 of the biomarkers listed in Table IV(C). Preferably, step (b) comprises or consists of measuring the expression of all of the biomarkers listed in Table IV(C).

Preferably, step (b) comprises or consists of measuring the expression in the test sample of all of the biomarkers defined in Table IV.

In one embodiment, the method is for differentiating between pancreatic cancer (PaC) and another disease state.

Preferably, step (b) comprises or consists of measuring the expression in the test sample of 1 or more biomarkers from the biomarkers listed in Table V(A), for example at least 2, 3, 4, 5, 6, 7, 8, 9 or 10 of the biomarkers listed in Table V(A). Preferably, step (b) also comprises or consists of measuring the expression in the test sample of 1 or more biomarkers from the biomarkers listed in Table V(B), for example at least 2, 3, 4, 5, 6, 7, 8, 9 10, 11, 12, 13, 14, 15, 16, 17, 18, 19, 20, 21, 22, 23 or 24 of the biomarkers listed in Table V(B). It is also preferred that step (b) comprises or consists of measuring the expression in the test sample of 1 or more biomarkers from the biomarkers listed in Table V(C), for example at least 2, 3, 4 or 5 of the biomarkers listed in Table V(C). Preferably, step (b) comprises or consists of measuring the expression in the test sample of 1 or more biomarkers from the biomarkers listed in Table V(D), for example at least 2 or 3 of the biomarkers listed in Table V(D). Preferably, step (b) comprises or consists of measuring the expression in the test sample of 1 or more biomarkers from the biomarkers listed in Table V(F), for example at least 2, 3, 4, 5 or 6 of the biomarkers listed in Table V(F). Preferably, step (b) comprises or consists of measuring the expression in the test sample of all of the biomarkers listed in Table V(A), Table V(B), Table V(C), Table V(D) and/or Table V(F).

By "differentiating between pancreatic cancer (PaC) and another disease state" we include differentiating between PaC and any other condition, including a state of health.

In one embodiment, the other disease state or states is chronic pancreatitis (ChP), acute inflammatory pancreatitis (AIP) and/or normal, for example, the other disease state or states may be chronic pancreatitis alone; acute inflammatory pancreatitis alone; chronic pancreatitis and acute inflammatory pancreatitis; chronic pancreatitis and normal; acute inflammatory pancreatitis and normal; or, chronic pancreatitis, acute inflammatory pancreatitis and normal.

When referring to a "normal" disease state we include individuals not afflicted with chronic pancreatitis (ChP) or acute inflammatory pancreatitis (AIP). Preferably the individuals are not afflicted with any pancreatic disease or disorder. Most preferably, the individuals are healthy individuals, i.e., they are not afflicted with any disease or disorder.

In a another embodiment, the method is for differentiating between pancreatic cancer and chronic pancreatitis (ChP). Preferably, step (b) comprises or consists of measuring the expression in the test sample of 1 or more biomarkers from the biomarkers listed in Table V(A), for example at least 2, 3, 4, 5, 6, 7, 8, 9 or 10 of the biomarkers listed in Table V(A). Step (b) may comprise or consist of measuring the expression in the test sample of 1 or more biomarkers from the biomarkers listed in Table V(C), for example at least 2, 3, 4 or 5 of the biomarkers listed in Table V(C). Step (b) may comprise or consist of measuring the expression in the test sample of all of the biomarkers listed in Table V(A) and/or Table V(C).

In an additional/alternative embodiment, the method is for differentiating between pancreatic cancer and acute inflammatory pancreatitis (AIP) and step (b) comprises or consists of measuring the expression in the test sample of 1 or more biomarkers from the biomarkers listed in Table V(A), for example at least 2, 3, 4, 5, 6, 7, 8, 9 or 10 of the biomarkers listed in Table V(A). Preferably, step (b) comprises or consists of measuring the expression in the test sample of 1 or more biomarkers from the biomarkers listed in Table V(B), for example at least 2, 3, 4, 5, 6, 7, 8, 9, 10, 11, 12, 13, 14, 15, 16, 17, 18, 19, 20, 21, 22, 23 or 24 of the biomarkers listed in Table V(B). Step (b) may comprise or consist of measuring the expression in the test sample of 1 or more biomarkers from the biomarkers listed in Table V(C), for example at least 2, 3, 4 or 5 of the biomarkers listed in Table V(C). Preferably, step (b) comprises or consists of measuring the expression in the test sample of 1 or more biomarkers from the biomarkers listed in Table V(E). Preferably, step (b) comprises or consists of measuring the expression in the test sample of 1 or more biomarkers from the biomarkers listed in Table V(F), for example at least 2, 3, 4, 5 or 6 of the biomarkers listed in Table V(F). Preferably, step (b) comprises or consists of measuring the expression in the test sample of 1 or more biomarkers from the biomarkers listed in Table V(H), for example at least 2 or 3 of the biomarkers listed in Table V(H). Hence, step (b) preferably comprises or consists of measuring the expression in the test sample of all of the biomarkers listed in Table V(A), Table V(B), Table V(C), Table V(E), Table V(F) and/or Table IV(H).

In one embodiment, the method is for differentiating between pancreatic cancer and normal (N). For a definition of "normal" disease state, see above. Preferably, step (b) comprises or consists of measuring the expression in the test sample of 1 or more biomarkers from the biomarkers listed in Table V(A), for example at least 2, 3, 4, 5, 6, 7, 8, 9 or 10 of the biomarkers listed in Table V(A). Preferably, step (b) comprises or consists of measuring the expression in the test sample of 1 or more biomarkers from the biomarkers listed in Table V(B), for example at least 2, 3, 4, 5, 6, 7, 8, 9, 10, 11, 12, 13, 14, 15, 16, 17, 18, 19, 20, 21, 22, 23 or 24 of the biomarkers listed in Table V(B). Preferably, step (b) comprises or consists of measuring the expression in the test sample of 1 or more biomarkers from the biomarkers listed in Table V(D), for example at least 2 or 3 of the biomarkers listed in Table V(D). Preferably, wherein step (b) comprises or consists of measuring the expression in the test sample of 1 or more biomarkers from the biomarkers listed in Table V(E). It is also preferred that step (b) comprises or consists of measuring the expression in the test sample of 1 or more biomarkers from the biomarkers listed in Table V(G), for example at least 2 or 3 of the biomarkers listed in Table V(G). Hence, step (b) may comprise or consist of measuring the expression in the test sample of all of the biomarkers listed in Table V(A), Table V(B), Table V(D), Table V(E) and/or Table IV(G).

In one embodiment, step (b) comprises or consists of measuring the expression of IL-3. In a further embodiment, step (b) comprises or consists of measuring the expression of Integrin α-10. In a still further embodiment, step (b) comprises or consists of measuring the expression of Mucin-1. In another embodiment, step (b) comprises or consists of measuring the expression of C1s. In an additional embodiment, step (b) comprises or consists of measuring the expression of MCP-3. In one embodiment, step (b) comprises or consists of measuring the expression of Angiomotin. In a further embodiment, step (b) comprises or consists of measuring the expression of BTK. In a still further embodiment, step (b) comprises or consists of measuring the expression of C1q. In another embodiment, step (b) comprises or consists of measuring the expression of CD40 ligand. In an additional embodiment, step (b) comprises or consists of measuring the expression of GM-CSF. In one embodiment, step (b) comprises or consists of measuring the expression of IgM. In a further embodiment, step (b) comprises or consists of measuring the expression of IL-11. In a still further embodiment, step (b) comprises or consists of measuring the expression of IL-16. In another embodiment, step (b) comprises or consists of measuring the expression of IL-1-ra. In an additional embodiment, step (b) comprises or consists of measuring the expression of IL-1α. In one embodiment, step (b) comprises or consists of measuring the expression of IL-1β. In a further embodiment, step (b) comprises or consists of measuring the expression of IL-2. In a still further embodiment, step (b) comprises or consists of measuring the expression of IL-7. In another embodiment, step (b) comprises or consists of measuring the expression of IL-9. In an additional embodiment, step (b) comprises or consists of measuring the expression of INF-γ. In one embodiment, step (b) comprises or consists of measuring the expression of Integrin α-11. In a further embodiment, step (b) comprises or consists of measuring the expression of JAK3. In a still further embodiment, step (b) comprises or consists of measuring the expression of Leptin. In another embodiment, step (b) comprises or consists of measuring the expression of Lewis γ. In an additional embodiment, step (b) comprises or consists of measuring the expression of MCP-4. In one embodiment, step (b) comprises or consists of measuring the expression of Procathepsin W. In a further embodiment, step (b) comprises or consists of measuring the expression of Properdin. In a still further embodiment, step (b) comprises or consists of measuring the expression of PSA. In another embodiment, step (b) comprises or consists of measuring the expression of RANTES. In an additional embodiment, step (b) comprises or consists of measuring the expression of Sialyl Lewis x. In one embodiment, step (b) comprises or consists of measuring the expression of TM peptide. In a further embodiment, step (b) comprises or consists of measuring the expression of TNF-α. In a still further embodiment, step (b) comprises or consists of measuring the expression of C4. In another embodiment, step (b) comprises or consists of measuring the expression of β-galactosidase.

In an additional embodiment, step (b) comprises or consists of measuring the expression of IL-12. In one embodiment, step (b) comprises or consists of measuring the expression of TGF-β1. In a further embodiment, step (b) comprises or consists of measuring the expression of VEGF. In a still further embodiment, step (b) comprises or consists of measuring the expression of IL-8. In another embodiment, step (b) comprises or consists of measuring the expression of C3. In an additional embodiment, step (b) comprises or consists of measuring the expression of IFN-γ. In one embodiment, step (b) comprises or consists of measuring the expression of IL-10. In a further embodiment, step (b) comprises or consists of measuring the expression of IL-13. In a still further embodiment, step (b) comprises or consists of measuring the expression of IL-18. In another embodiment, step (b) comprises or consists of measuring the expression of IL-6. In an additional embodiment, step (b) comprises or consists of measuring the expression of Lewis x. In one embodiment, step (b) comprises or consists of measuring the expression of Eotaxin. In a further embodiment, step (b) comprises or consists of measuring the expression of C1 esterase inhibitor. In a still further embodiment, step (b) comprises or consists of measuring the expression of MCP-1. In another embodiment, step (b) comprises or consists of measuring the expression of TNF-β. In an additional embodiment, step (b) comprises or consists of measuring the expression of GLP-1. In one embodiment, step (b) comprises or consists of measuring the expression of IL-5. In a further embodiment, step (b) comprises or consists of measuring the expression of IL-4. In a still further embodiment, step (b) comprises or consists of measuring the expression of Factor B. In another embodiment, step (b) comprises or consists of measuring the expression of C5. In an additional embodiment, step (b) comprises or consists of measuring the expression of CD40.

In one embodiment, step (b) does not comprise measuring the expression of IL-3. In a further embodiment, step (b) does not comprise measuring the expression of Integrin a-10. In a still further embodiment, step (b) does not comprise measuring the expression of Mucin-1. In another embodiment, step (b) does not comprise measuring the expression of C1s. In an additional embodiment, step (b) does not comprise measuring the expression of MCP-3. In one embodiment, step (b) does not comprise measuring the expression of Angiomotin. In a further embodiment, step (b) does not comprise measuring the expression of BTK. In a still further embodiment, step (b) does not comprise measuring the expression of C1q. In another embodiment, step (b) does not comprise measuring the expression of CD40 ligand. In an additional embodiment, step (b) does not comprise measuring the expression of GM-CSF. In one embodiment, step (b) does not comprise measuring the expression of IgM. In a further embodiment, step (b) does not comprise measuring the expression of IL-11. In a still further embodiment, step (b) does not comprise measuring the expression of IL-16. In another embodiment, step (b) does not comprise measuring the expression of IL-1-ra. In an additional embodiment, step (b) does not comprise measuring the expression of IL-1α. In one embodiment, step (b) does not comprise measuring the expression of IL-1β. In a further embodiment, step (b) does not comprise measuring the expression of IL-2. In a still further embodiment, step (b) does not comprise measuring the expression of IL-7. In another embodiment, step (b) does not comprise measuring the expression of IL-9. In an additional embodiment, step (b) does not comprise measuring the expression of INF-γ. In one embodiment, step (b) does not comprise measuring the expression of Integrin α-11. In a further embodiment, step (b) does not comprise measuring the expression of JAK3. In a still further embodiment, step (b) does not comprise measuring the expression of Leptin. In another embodiment, step (b) does not comprise measuring the expression of Lewis γ. In an additional embodiment, step (b) does not comprise measuring the expression of MCP-4. In one embodiment, step (b) does not comprise measuring the expression of Procathepsin W. In a further embodiment, step (b) does not comprise measuring the expression of Properdin. In a still further embodiment, step (b) does not comprise measuring the expression of PSA. In another embodiment, step (b) does not comprise measuring the expression of RANTES. In an additional embodiment, step (b) does not comprise measuring the expression of Sialyl Lewis x. In one embodiment, step (b) does not comprise measuring the expression of TM peptide. In a further embodiment, step (b) does not comprise measuring the expression of TNF-α. In a still further embodiment, step (b) does not comprise measuring the expression of C4.

In another embodiment, step (b) does not comprise measuring the expression of β-galactosidase.

In an additional embodiment, step (b) does not comprise measuring the expression of IL-12. In one embodiment, step (b) does not comprise measuring the expression of TGF-β1. In a further embodiment, step (b) does not comprise measuring the expression of VEGF. In a still further embodiment, step (b) does not comprise measuring the expression of IL-8. In another embodiment, step (b) does not comprise measuring the expression of C3. In an additional embodiment, step (b) does not comprise measuring the expression of IFN-γ. In one embodiment, step (b) does not comprise measuring the expression of IL-10. In a further embodiment, step (b) does not comprise measuring the expression of IL-13. In a still further embodiment, step (b) does not comprise measuring the expression of IL-18. In another embodiment, step (b) does not comprise measuring the expression of IL-6. In an additional embodiment, step (b) does not comprise measuring the expression of Lewis x. In one embodiment, step (b) does not comprise measuring the expression of Eotaxin. In a further embodiment, step (b) does not comprise measuring the expression of C1 esterase inhibitor. In a still further embodiment, step (b) does not comprise measuring the expression of MCP-1. In another embodiment, step (b) does not comprise measuring the expression of TNF-β. In an additional embodiment, step (b) does not comprise measuring the expression of GLP-1. In one embodiment, step (b) does not comprise measuring the expression of IL-5. In a further embodiment, step (b) does not comprise measuring the expression of IL-4. In a still further embodiment, step (b) does not comprise measuring the expression of Factor B. In another embodiment, step (b) does not comprise measuring the expression of C5. In an additional embodiment, step (b) does not comprise measuring the expression of CD40.

By "TM peptide" we mean a peptide derived from a 10TM protein, to which the scFv antibody construct of SEQ ID NO: 1 below has specificity (wherein the CDR sequences are indicated by bold, italicised text):

[SEQ ID NO: 1]
MAEVQLLESGGGLVQPGGSLRLSCAASGFTFSSYGFHWVRQAPGK

GLEWVSLISWDGGSTYYADSVKGRFTISRDNSKNTLYLQMNSL

RAEDTAVYYCARGTWFDPWGQGTLVTVSSGGGGSGGGGSGGGGSQSVL

TQPPSASGTPGQRVTISCSGSSSNIGNNAVNWYQQLPGTAPKLL

IYRNNQRPSGVPDRFSGSKSGTSASLAISGLRSEDEADYY

CAAWDDSLSWVFGGGTKLTVLG

Hence, this scFv may be used or any antibody, or antigen binding fragment thereof, that competes with this scFv for binding to the 10TM protein. For example, the antibody, or antigen binding fragment thereof, may comprise the same CDRs as present in SEQ ID NO: 1.

It will be appreciated by persons skilled in the art that such an antibody may be produced with an affinity tag (e.g. at the C-terminus) for purification purposes. For example, an affinity tag of SEQ ID NO: 2 below may be utilised:

DYKDHDGDYKDHDIDYKDDDDKAAAHHHHHH    [SEQ ID NO: 2]

In one embodiment, presence of pancreatic cancer is identified in the event that the expression in the test sample of IL-3, Integrinα-10, Mucin-1, C1s, GLP-1R, MCP-3, Angiomotin, BTK, CD40 ligand, GM-CSF, IgM, IL-11, IL-16, IL-1-ra, IL-1α, IL-1β, IL-2, IL-7, IL-9, INF-γ, Integrinα-11, JAK3, Leptin, Lewis y, MCP-4, Procathepsin W, PSA, RANTES, Sialyl Lewis x, TM peptide, TNF-α, C4, β-galactosidase, IL-12, TGF-β1, VEGF, IL-8, C3, IFN-γ, IL-10, IL-13, IL-18, IL-6, Lewis x, Eotaxin, C1 esterase inhibitor, MCP-1, TNF-β, GLP-1, IL-5, IL-4, Factor B, C5 and/or CD40 are up regulated compared to the negative control(s) and/or corresponds to the expression of positive control(s).

In another embodiment, presence of pancreatic cancer is identified in the event that the expression in the last sample of C1q and/or Properdin is down regulated compared to the negative control(s) and/or corresponds to the expression of positive control(s). Generally, diagnosis is made with an ROC AUC of at least 0.55, for example with an ROC AUC of at least, 0.60, 0.65, 0.70, 0.75, 0.80, 0.85, 0.90, 0.95, 0.96, 0.97, 0.98, 0.99 or with an ROC AUC of 1.00. Preferably, diagnosis is made with an ROC AUC of at least 0.85, and most preferably with an ROC AUC of 1.

Typically, diagnosis is performed using a support vector machine (SVM), such as those available from http://cran.r-project.org/web/packages/e1071/index.html (e.g. e1071 1.5-24). However, any other suitable means may also be used.

Support vector machines (SVMs) are a set of related supervised learning methods used for classification and regression. Given a set of training examples, each marked as belonging to one of two categories, an SVM training algorithm builds a model that predicts whether a new example falls into one category or the other. Intuitively, an SVM model is a representation of the examples as points in space, mapped so that the examples of the separate categories are divided by a clear gap that is as wide as possible. New examples are then mapped into that same space and predicted to belong to a category based on which side of the gap they fall on.

More formally, a support vector machine constructs a hyperplane or set of hyperplanes in a high or infinite dimensional space, which can be used for classification, regression or other tasks. Intuitively, a good separation is achieved by the hyperplane that has the largest distance to the nearest training datapoints of any class (so-called functional margin), since in general the larger the margin the lower the generalization error of the classifier. For more information on SVMs, see for example, Burges, 1998, *Data Mining and Knowledge Discovery*, 2:121-167.

In one embodiment of the invention, the SVM is 'trained' prior to performing the methods of the invention using biomarker profiles from individuals with known disease status (for example, individuals known to have pancreatic cancer, individuals known to have acute inflammatory pancreatitis, individuals known to have chronic pancreatitis or individuals known to be healthy). By running such training samples, the SVM is able to learn what biomarker profiles are associated with pancreatic cancer. Once the training process is complete, the SVM is then able whether or not the biomarker sample tested is from an individual with pancreatic cancer.

However, this training procedure can be by-passed by pre-programming the SVM with the necessary training parameters. For example, diagnoses can be performed according to the known SVM parameters using the SVM algorithm detailed in Table V, based on the measurement of any or all of the biomarkers listed in Table III or Table IV. negative control(s) and/or corresponds to the expression of positive control(s).

It will be appreciated by skilled persons that suitable SVM parameters can be determined for any combination of the biomarkers listed in Table III or Table IV by training an SVM machine with the appropriate selection of data (i.e. biomarker measurements from individuals with known pancreatic cancer status).

Preferably, the method of the invention has an accuracy of at least 60%, for example 61%, 62%, 63%, 64%, 65%, 66%, 67%, 68%, 69%, 70%, 71%, 72%, 73%, 74%, 75%, 76%, 77%, 78%, 79%, 80%. 81%, 82%, 83%, 84%, 85%, 86%, 87%, 88%, 89%, 90%, 91%, 92%, 93%, 94%, 95%, 96%, 97%, 98%, 99% or 100% accuracy.

Preferably, the method of the invention has a sensitivity of at least 60%, for example 61%, 62%, 63%, 64%, 65%, 66%, 67%, 68%, 69%, 70%, 71%, 72%, 73%, 74%, 75%, 76%, 77%, 78%, 79%, 80%. 81%, 82%, 83%, 84%, 85%, 86%, 87%, 88%, 89%, 90%, 91%, 92%, 93%, 94%, 95%, 96%, 97%, 98%, 99% or 100% sensitivity.

Preferably, the method of the invention has a specificity of at least 60%, for example 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99% or 100% specificity.

By "accuracy" we mean the proportion of correct outcomes of a method, by "sensitivity" we mean the proportion of all PaC positive sample that are correctly classified as positives, and by "specificity" we mean the proportion of all PaC negative samples that are correctly classified as negatives.

In one embodiment, the individual not afflicted with pancreatic cancer is not afflicted with pancreatic cancer (PaC), chronic pancreatitis (ChP) or acute inflammatory pancreatitis (AIP). More preferably, the healthy individual is not afflicted with any pancreatic disease or condition. Even more preferably, the individual not afflicted with pancreatic cancer is not afflicted with any disease or condition. Most preferably, the individual not afflicted with pancreatic cancer is a healthy individual. By a "healthy individual" we include individuals considered by a skilled person to be physically vigorous and free from physical disease.

However, in another embodiment the individual not afflicted with pancreatic cancer is afflicted with chronic pancreatitis. In still another embodiment, the individual not afflicted with pancreatic cancer is afflicted with acute inflammatory pancreatitis.

As previously mentioned the present method is for determining the presence of pancreatic cancer in an individual. In one embodiment the pancreatic cancer is selected from the group consisting of adenocarcinoma, adenosquamous carcinoma, signet ring cell carcinoma, hepatoid carcinoma, colloid carcinoma, undifferentiated carcinoma, and undifferentiated carcinomas with osteoclast-like giant cells. Preferably, the pancreatic cancer is a pancreatic adenocarcinoma. More preferably, the pancreatic cancer is pancreatic ductal adenocarcinoma, also known as exocrine pancreatic cancer.

In a further embodiment, step (b), (d) and/or step (f) is performed using a first binding agent capable of binding to the one or more biomarkers. It will be appreciated by persons skilled in the art that the first binding agent may comprise or consist of a single species with specificity for one of the protein biomarkers or a plurality of different species, each with specificity for a different protein biomarker.

Suitable binding agents (also referred to as binding molecules) can be selected from a library, based on their ability to bind a given motif, as discussed below.

At least one type of the binding agents, and more typically all of the types, may comprise or consist of an antibody or antigen-binding fragment of the same, or a variant thereof.

Methods for the production and use of antibodies are well known in the art, for example see *Antibodies: A Laboratory Manual*, 1988, Harlow & Lane, Cold Spring Harbor Press, ISBN-13: 978-0879693145, *Using Antibodies: A Laboratory Manual*, 1998, Harlow & Lane. Cold Spring Harbor Press, ISBN-13: 978-0879695446 and *Making and Using Antibodies: A Practical Handbook*, 2006, Howard & Kaser, CRC Press, ISBN-13: 978-0849335280 (the disclosures of which are incorporated herein by reference).

Thus, a fragment may contain one or more of the variable heavy ($V_H$) or variable light ($V_L$) domains. For example, the term antibody fragment includes Fab-like molecules (Better et al (1988) *Science* 240, 1041); Fv molecules (Skerra et al (1988) *Science* 240, 1038); single-chain Fv (ScFv) molecules where the $V_H$ and $V_L$ partner domains are linked via a flexible oligopeptide (Bird et al (1988) *Science* 242, 423; Huston et al (1988) *Proc. Natl. Acad. Sci. USA* 85, 5879) and single domain antibodies (dAbs) comprising isolated V domains (Ward et al (1989) *Nature* 341, 544).

The term "antibody variant" includes any synthetic antibodies, recombinant antibodies or antibody hybrids, such as but not limited to, a single-chain antibody molecule produced by phage-display of immunoglobulin light and/or heavy chain variable and/or constant regions, or other immunointeractive molecule capable of binding to an antigen in an immunoassay format that is known to those skilled in the art.

A general review of the techniques involved in the synthesis of antibody fragments which retain their specific binding sites is to be found in Winter & Milstein (1991) *Nature* 349, 293-299.

Molecular libraries such as antibody libraries (Clackson et al, 1991, *Nature* 352, 624-628; Marks et al, 1991, *J Mol Biol* 222(3): 581-97), peptide libraries (Smith, 1985, *Science* 228(4705): 1315-7), expressed cDNA libraries (Santi et al (2000) *J Mol Biol* 296(2): 497-508) libraries on other scaffolds than the antibody framework such as affibodies (Gunneriusson et al, 1999, *Appl Environ Microbiol* 65(9): 4134-40) or libraries based on aptamers (Kenan et al, 1999, *Methods Mol Biol* 118, 217-31) may be used as a source from which binding molecules that are specific for a given motif are selected for use in the methods of the invention.

The molecular libraries may be expressed in vivo in prokaryotic (Clackson et al, 1991, *op. cit.;* Marks et al, 1991, *op. cit.*) or eukaryotic cells (Kieke et al, 1999, *Proc Natl Acad Sci U.S.A.*, 96(10):5651-6) or may be expressed in vitro without involvement of cells (Hanes & Pluckthun, 1997, *Proc Natl Acad Sci USA* 94(10):4937-42; He & Taussig, 1997, *Nucleic Acids Res* 25(24):5132-4; Nemoto et al, 1997, *FEBS Lett*, 414(2):405-8).

In cases when protein based libraries are used often the genes encoding the libraries of potential binding molecules are packaged in viruses and the potential binding molecule is displayed at the surface of the virus (Clackson et al, 1991, *op. cit.;* Marks et al, 1991, *op. cit;* Smith, 1985, op. cit.).

The most commonly used such system today is filamentous bacteriophage displaying antibody fragments at their surfaces, the antibody fragments being expressed as a fusion to the minor coat protein of the bacteriophage (Clackson et al, 1991, *op. cit.;* Marks et al, 1991, *op. cit*). However, also other systems for display using other viruses (EP 39578), bacteria (Gunneriusson et al, 1999, *op. cit.;* Daugherty et al, 1998, *Protein Eng* 11(9):825-32; Daugherty et al, 1999, *Protein Eng* 12(7):613-21), and yeast (Shusta of et al, 1999, *J Mol Biol* 292(5):949-56) have been used.

In addition, display systems have been developed utilising linkage of the polypeptide product to its encoding mRNA in so called ribosome display systems (Hanes & Pluckthun, 1997, *op. cit.;* He & Taussig, 1997, *op. cit.;* Nemoto et al, 1997, *op. cit.*), or alternatively linkage of the polypeptide product to the encoding DNA (see U.S. Pat. No. 5,856,090 and WO 98/37186).

When potential binding molecules are selected from libraries one or a few selector peptides having defined motifs are usually employed. Amino acid residues that provide structure, decreasing flexibility in the peptide or charged, polar or hydrophobic side chains allowing interaction with the binding molecule may be used in the design of motifs for selector peptides.

For example:
(i) Proline may stabilise a peptide structure as its side chain is bound both to the alpha carbon as well as the nitrogen;
(ii) Phenylalanine, tyrosine and tryptophan have aromatic side chains and are highly hydrophobic, whereas leucine and isoleucine have aliphatic side chains and are also hydrophobic;
(iii) Lysine, arginine and histidine have basic side chains and will be positively charged at neutral pH, whereas aspartate and glutamate have acidic side chains and will be negatively charged at neutral pH;
(iv) Asparagine and glutamine are neutral at neutral pH but contain a amide group which may participate in hydrogen bonds;
(v) Serine, threonine and tyrosine side chains contain hydroxyl groups, which may participate in hydrogen bonds.

Typically, selection of binding agents may involve the use of array technologies and systems to analyse binding to spots corresponding to types of binding molecules.

In one embodiment, the first binding agent(s) is/are immobilised on a surface (e.g. on a multiwell plate or array).

The variable heavy ($V_H$) and variable light ($V_L$) domains of the antibody are involved in antigen recognition, a fact first recognised by early protease digestion experiments. Further confirmation was found by "humanisation" of rodent antibodies. Variable domains of rodent origin may be fused to constant domains of human origin such that the resultant antibody retains the antigenic specificity of the rodent parented antibody (Morrison et al (1984) *Proc. Natl. Acad. Sci. USA* 81, 6851-6855).

That antigenic specificity is conferred by variable domains and is independent of the constant domains is known from experiments involving the bacterial expression of antibody fragments, all containing one or more variable domains. These molecules include Fab-like molecules (Better et al (1988) *Science* 240, 1041); Fv molecules (Skerra et al (1988) *Science* 240, 1038); single-chain Fv (ScFv) molecules where the $V_H$ and $V_L$ partner domains are linked via a flexible oligopeptide (Bird et al (1988) *Science* 242, 423; Huston et al (1988) *Proc. Natl. Acad. Sci. USA* 85, 5879) and single domain antibodies (dAbs) comprising isolated V domains (Ward et al (1989) *Nature* 341, 544). A general review of the techniques involved in the synthesis of antibody fragments which retain their specific binding sites is to be found in Winter & Milstein (1991) *Nature* 349, 293-299.

By "ScFv molecules" we mean molecules wherein the $V_H$ and $V_L$ partner domains are linked via a flexible oligopeptide.

The advantages of using antibody fragments, rather than whole antibodies, are several-fold. The smaller size of the fragments may lead to improved pharmacological properties, such as better penetration of solid tissue. Effector functions of whole antibodies, such as complement binding, are removed. Fab, Fv, ScFv and dAb antibody fragments can all be expressed in and secreted from E. coli, thus allowing the facile production of large amounts of the said fragments.

Whole antibodies, and F(ab')$_2$ fragments are "bivalent". By "bivalent" we mean that the said antibodies and F(ab')$_2$ fragments have two antigen combining sites. In contrast, Fab, Fv, ScFv arid dAb fragments are monovalent, having only one antigen combining sites.

The antibodies may be monoclonal or polyclonal. Suitable monoclonal antibodies may be prepared by known techniques, for example those disclosed in "Monoclonal Antibodies: A manual of techniques", H Zola (CRC Press, 1988) and in "Monoclonal Hybridoma Antibodies: Techniques and applications", J G R Hurrell (CRC Press, 1982), both of which are incorporated herein by reference.

In one embodiment, the first binding agent immobilised on a surface (e.g. on a multiwell plate or array).

The variable heavy ($V_H$) and variable light ($V_L$) domains of the antibody are involved in antigen recognition, a fact first recognised by early protease digestion experiments. Further confirmation was found by "humanisation" of rodent antibodies. Variable domains of rodent origin may be fused to constant domains of human origin such that the resultant antibody retains the antigenic specificity of the rodent parented antibody (Morrison et al (1984) Proc. Natl. Acad. Sci. USA 81, 6851-6855).

That antigenic specificity is conferred by variable domains and is independent of the constant domains is known from experiments involving the bacterial expression of antibody fragments, all containing one or more variable domains. These molecules include Fab-like molecules (Better et al (1988) Science 240, 1041); Fv molecules (Skerra et al (1988) Science 240, 1038); single-chain Fv (ScFv) molecules where the $V_H$ and $V_L$ partner domains are linked via a flexible oligopeptide (Bird et al (1988) Science 242, 423; Huston et al (1988) Proc. Natl. Acad. Sci. USA 85, 5879) and single domain antibodies (dAbs) comprising isolated V domains (Ward et al (1989) Nature 341, 544). A general review of the techniques involved in the synthesis of antibody fragments which retain their specific binding sites is to be found in Winter & Milstein (1991) Nature 349, 293-299.

By "ScFv molecules" we mean molecules wherein the $V_H$ and $V_L$ partner domains are linked via a flexible oligopeptide.

The advantages of using antibody fragments, rather than whole antibodies, are several-fold. The smaller size of the fragments may lead to improved pharmacological properties, such as better penetration of solid tissue. Effector functions of whole antibodies, such as complement binding, are removed. Fab, Fv, ScFv and dAb antibody fragments can all be expressed in and secreted from *E. coli*, thus allowing the facile production of large amounts of the said fragments.

Whole antibodies, and F(ab')$_2$ fragments are "bivalent". By "bivalent" we mean that the said antibodies and F(ab')$_2$ fragments have two antigen combining sites. In contrast, Fab, Fv, ScFv and dAb fragments are monovalent, having only one antigen combining sites.

The antibodies may be monoclonal or polyclonal. Suitable monoclonal antibodies may be prepared by known techniques, for example those disclosed in "Monoclonal Antibodies: A manual of techniques", H Zola (CRC Press, 1988) and in "Monoclonal Hybridoma Antibodies: Techniques and applications", J G R Hurrell (CRC Press, 1982), both of which are incorporated herein by reference.

Hence, the first binding agent may comprise or consist of an antibody or an antigen-binding fragment thereof. Preferably, the antibody or antigen-binding fragment thereof is a recombinant antibody or antigen-binding fragment thereof. The antibody or antigen-binding fragment thereof may be selected from the group consisting of: scFv, Fab, and a binding domain of an immunoglobulin molecule.

Preferably, the first binding agent is immobilised on a surface.

The one or more biomarkers in the test sample may be labelled with a detectable moiety.

By a "detectable moiety" we include the meaning that the moiety is one which may be detected and the relative amount and/or location of the moiety (for example, the location on an array) determined.

Suitable detectable moieties are well known in the art.

Thus, the detectable moiety may be a fluorescent and/or luminescent and/or chemiluminescent moiety which, when exposed to specific conditions, may be detected. For example, a fluorescent moiety may need to be exposed to radiation (i.e. light) at a specific wavelength and intensity to cause excitation of the fluorescent moiety, thereby enabling it to emit detectable fluorescence at a specific wavelength that may be detected.

Alternatively, the detectable moiety may be an enzyme which is capable of converting a (preferably undetectable) substrate into a detectable product that can be visualised and/or detected. Examples of suitable enzymes are discussed in more detail below in relation to, for example, ELISA assays.

Alternatively, the detectable moiety may be a radioactive atom which is useful in imaging. Suitable radioactive atoms include $^{99m}$Tc and $^{123}$I for scintigraphic studies. Other readily detectable moieties include, for example, spin labels for magnetic resonance imaging (MRI) such as $^{123}$I again, $^{131}$I, $^{111}$In, $^{19}$F, $^{13}$C, $^{15}$N, $^{17}$O, gadolinium, manganese or iron. Clearly, the agent to be detected (such as, for example, the one or more biomarkers in the test sample and/or control sample described herein and/or an antibody molecule for use in detecting a selected protein) must have sufficient of the appropriate atomic isotopes in order for the detectable moiety to be readily detectable.

The radio- or other labels may be incorporated into the agents of the invention (i.e. the proteins present in the samples of the methods of the invention and/or the binding agents of the invention) in known ways. For example, if the binding moiety is a polypeptide it may be biosynthesised or may be synthesised by chemical amino acid synthesis using suitable amino acid precursors involving, for example, fluorine-19 in place of hydrogen. Labels such as $^{99m}$Tc, $^{123}$I, $^{186}$Rh, and $^{111}$In can, for example, be attached via cysteine residues in the binding moiety. Yttrium-90 can be attached via a lysine residue. The IODOGEN method (Fraker et al (1978) Biochem. Biophys. Res. Comm. 80, 49-57) can be used to incorporate $^{123}$I. Reference ("Monoclonal Antibodies in Imrnunoscintigraphy", J-F Chatal, CRC Press, 1989) describes other methods in detail. Methods for conjugating other detectable moieties (such as enzymatic, fluorescent, luminescent, chemiluminescent or radioactive moieties) to proteins are well known in the art.

Preferably, the one or more biomarkers in the control sample(s) are labelled with a detectable moiety. The detectable moiety may be selected from the group consisting of: a fluorescent moiety; a luminescent moiety; a chemiluminescent moiety; a radioactive moiety; an enzymatic moiety. However, it is preferred that the detectable moiety is biotin.

In an additional embodiment step (b), (d) and/or step (f) is performed using an assay comprising a second binding agent capable of binding to the one or more biomarkers, the second binding agent comprising a detectable moiety. Preferably, the second binding agent comprises or consists of an antibody or an antigen-binding fragment thereof. Preferably, the antibody or antigen-binding fragment thereof is a recombinant antibody or antigen-binding fragment thereof. Most preferably, the antibody or antigen-binding fragment thereof is selected from the group consisting of: scFv, Fab and a binding domain of an immunoglobulin molecule. In one embodiment the detectable moiety is selected from the group consisting of: a fluorescent moiety; a luminescent moiety; a chemiluminescent moiety; a radioactive moiety and an enzymatic moiety. Preferably, the detectable moiety is fluorescent moiety (for example an Alexa Fluor dye, e.g. Alexa647).

In one embodiment, the method of the first aspect of the invention comprises or consists of an ELISA (Enzyme Linked Immunosorbent Assay).

Preferred assays for detecting serum or plasma proteins include enzyme linked immunosorbent assays (ELISA), radioimmunoassay (RIA), immunoradiometric assays (IRMA) and immunoenzymatic assays (IEMA), including sandwich assays using monoclonal and/or polyclonal antibodies. Exemplary sandwich assays are described by David et al in U.S. Pat. Nos. 4,376,110 and 4,486.530, hereby incorporated by reference. Antibody staining of cells on slides may be used in methods well known in cytology laboratory diagnostic tests, as well known to those skilled in the art.

Typically, the assay is an ELISA (Enzyme Linked Immunosorbent Assay) which typically involves the use of enzymes giving a coloured reaction product, usually in solid phase assays. Enzymes such as horseradish peroxidase and phosphatase have been widely employed. A way of amplifying the phosphatase reaction is to use NADP as a substrate to generate NAD which now acts as a coenzyme for a second enzyme system. Pyrophosphatase from *Escherichia coli* provides a good conjugate because the enzyme is not present in tissues, is stable and gives a good reaction colour. Chemi-luminescent systems based on enzymes such as luciferase can also be used.

ELISA methods are well known in the art, for example see The ELISA Guidebook (Methods in Molecular Biology), 2000, Crowther, Humana Press, ISBN-13: 978-0896037281 (the disclosures of which are incorporated by reference).

Conjugation with the vitamin biotin is frequently used since this can readily be detected by its reaction with enzyme-linked avidin or streptavidin to which it binds with great specificity and affinity.

However, step (b), (d) and/or step (f) is alternatively performed using an array. Arrays per se are well known in the art. Typically they are formed of a linear or two-dimensional structure having spaced apart (i.e. discrete) regions ("spots"), each having a finite area, formed on the surface of a solid support. An array can also be a bead structure where each bead can be identified by a molecular code or colour code or identified in a continuous flow. Analysis can also be performed sequentially where the sample is passed over a series of spots each adsorbing the class of molecules from the solution. The solid support is typically glass or a polymer, the most commonly used polymers being cellulose, polyacrylamide, nylon, polystyrene, polyvinyl chloride or polypropylene. The solid supports may be in the form of tubes, beads, discs, silicon chips, microplates, polyvinylidene difluoride (PVDF) membrane, nitrocellulose membrane, nylon membrane, other porous membrane, non-porous membrane (e.g. plastic, polymer, perspex, silicon, amongst others), a plurality of polymeric pins, or a plurality of microtitre wells, or any other surface suitable for immobilising proteins, polynucleotides and other suitable molecules and/or conducting an immunoassay. The binding processes are well known in the art and generally consist of cross-linking covalently binding or physically adsorbing a protein molecule, polynucleotide or the like to the solid support. By using well-known techniques, such as contact or non-contact printing, masking or photolithography, the location of each spot can be defined. For reviews see Jenkins, R. E., Pennington, S. R. (2001, *Proteomics*, 2,13-29) and Lal et al (2002, *Drug Discov Today* 15;7(18 Suppl):S143-9).

Typically the array is a microarray. By "microarray" we include the meaning of an array of regions having a density of discrete regions of at least about 100/cm$^2$, and preferably at least about 1000/cm2. The regions in a microarray have typical dimensions, e.g., diameters, in the range of between about 10-250 µm, and are separated from other regions in the array by about the same distance. The array may also be a macroarray or a nanoarray.

Once suitable binding molecules (discussed above) have been identified and isolated, the skilled person can manufacture an array using methods well known in the art of molecular biology.

Hence, the array may be the array is a bead-based array or a surface-based array.

Preferably, the array is selected from the group consisting of: macroarray, microarray and nanoarray.

In one embodiment, the method according to the first aspect of the invention comprises:
(i) labelling biomarkers present in the sample with biotin;
(ii) contacting the biotin-labelled proteins with an array comprising a plurality of scFv immobilised at discrete locations on its surface, the scFv having specificity for one or more of the proteins in Table III;
(iii) contacting the immobilised scFv with a streptavidin conjugate comprising a fluorescent dye; and
(iv) detecting the presence of the dye at discrete locations on the array surface
wherein the expression of the dye on the array surface is indicative of the expression of a biomarker from Table III in the sample.

In an alternative embodiment step (b), (d) and/or (f) comprises measuring the expression of a nucleic acid molecule encoding the one or more biomarkers. Preferably the nucleic acid molecule is a cDNA molecule or an mRNA molecule. Most preferably the nucleic acid molecule is an mRNA molecule.

Hence the expression of the one or more biomarker(s) in step (b), (d) and/or (f) may be performed using a method selected from the group consisting of Southern hybridisation, Northern hybridisation, polymerase chain reaction (PCR), reverse transcriptase PCR (RT-PCR), quantitative real-time PCR (qRT-PCR), nanoarray, microarray, macroarray, autoradiography and in situ hybridisation. Preferably, the expression of the one or more biomarker(s) in step (b) is determined using a DNA microarray.

In one embodiment, the measuring of the expression of the one or more biomarker(s) in step (b), (d) and/or (f) is performed using one or more binding moieties, each individually capable of binding selectively to a nucleic acid molecule encoding one of the biomarkers identified in Table III.

In a further embodiment, the one or more binding moieties each comprise or consist of a nucleic acid molecule. Thus, the one or more binding moieties may each comprise or consist of DNA, RNA, PNA, LNA, GNA, TNA or PMO. However, it is preferred that the one or more binding moieties each comprise or consist of DNA.

Preferably, the one or more binding moieties are 5 to 100 nucleotides in length. More preferably, the one or more nucleic acid molecules are 15 to 35 nucleotides in length. More preferably still, the binding moiety comprises a detectable moiety.

In an additional embodiment, the detectable moiety is selected from the group consisting of: a fluorescent moiety; a luminescent moiety; a chemiluminescent moiety; a radioactive moiety (for example, a radioactive atom); and an enzymatic moiety. Preferably, the detectable moiety comprises or consists of a radioactive atom. The radioactive atom may be selected from the group consisting of technetium-99m, iodine-123, iodine-125, iodine-131, indium-111, fluorine-19, carbon-13, nitrogen-15, oxygen-17, phosphorus-32, sulphur-35, deuterium, tritium, rhenium-186, rhenium-188 and yttrium-90.

However, the detectable moiety of the binding moiety may be a fluorescent moiety (for example an Alexa Fluor dye, e.g. Alexa647).

In one embodiment the sample provided in step (b), (d) and/or (f) is selected from the group consisting of unfractionated blood, plasma, serum, tissue fluid, pancreatic tissue, pancreatic juice, bile and urine. Preferably, the sample provided in step (b), (d) and/or (f) is selected from the group consisting of unfractionated blood, plasma and serum. More preferably, the sample provided in step (b), (d) and/or (f) is plasma. In another preferred embodiment, the sample provided in step (b), (d) and/or (1) is serum.

A second aspect of the present invention provides an array for determining the presence of pancreatic cancer in an individual comprising one or more binding agent as defined in the first aspect of the present invention.

Arrays suitable for use in the methods of the invention are discussed above.

Preferably the one or more binding agents are capable of binding to all of the proteins defined in Table III.

A third aspect of the present invention provides the use of one or more biomarkers selected from the group defined in the first aspect of the invention as a diagnostic marker for determining the presence of pancreatic cancer in an individual. Preferably, all of the proteins defined in Table III are used as diagnostic markers for determining the presence of pancreatic cancer in an individual.

A fourth aspect of the present invention provides a kit for determining the presence of pancreatic cancer comprising:
A) one or more first binding agent according to the first aspect of the invention or an array according the second aspect of the invention; and
B) instructions for performing the method according to the first aspect of the invention.

Preferred, non-limiting examples which embody certain aspects of the invention will now be described, with reference to the following tables and figures:

FIG. 1: Classification of PaC vs. N

A) Scanned image of an antibody microarray hybridized with a PaC serum. In total, 160 probes, including position markers and controls, were printed in eight 20×8 subarrays per slide. B) Differentially expressed (p<0.05) serum analytes for PaC vs. N. C) ROC curve for PaC vs. N based on all antibodies, i.e. using unfiltered data. D) Classification of PaC vs. N, using the SVM prediction values based on all antibodies (red dots-PaC, blue dots-N). The relative expression levels of the top 20 differentially expressed (p<0.02) non-redundant analytes are shown in a heatmap. Red—upregulated, green—down-regulated, black—equal levels. (E) Validation of scFv antibody specificity, illustrated for a highly differentially expressed (p=0.005) analyte, IL-6, using a 278 human protein array. (F) Validation of scFv antibody specificity, illustrated for a modestly differentially expressed (p=0.04) analyte, IL-10, using a 278 human protein array.

FIG. 2: Pre-validation of biomarker signature for PaC vs. N classification (A) Condensation of the biomarker signature for PaC vs. N classification in the first patient cohort using a LOO procedure combined with a backward elimination strategy. The observed ROC AUC values were plotted against the remaining number of antibodies. (B) The condensed 18-analyte non-redundant biomarker signature obtained from the first patient cohort. (C) The first patient cohort was used as training set, and the output classifier was then tested on a new, independent patient group, the second patient cohort. (D) Pre-validation of the biomarker signature for PaC vs. N classification illustrated by the ROC curve obtained for the classifier on the test set.

FIG. 3: Candidate serum biomarker signatures differentiating PaC and pancreatitis (A) Differentially expressed (p<0.05) serum analytes for PaC vs. ChP, AIP or ChP+AIP+N, respectively. (B) ROC curves for PaC vs ChP, AIP, or ChP+AIP+N classification based on all antibodies, i.e. using unfiltered data. (C) Validation of the antibody microarray data of selected analytes using a 10-plex cytokine sandwich antibody microarray (MSD). Data is only shown for the only analyte, IL-8, for which the majority of the observed signals were above the lower limit of detection for the MSD assay.

FIG. 4: Pre-validation of a candidate serum biomarker signature for PaC diagnosis (A) The first patient cohort, composed of PaC, N, ChP and AIP, was split into a training set (two thirds) and a test set (one third). (B) The condensed 25 non-redundant serum biomarker signature obtained for the training set using a backward elimination strategy. (C) Pre-validation of the condensed 25-analyte biomarker signature for PaC diagnosis, as illustrated by the ROC curve obtained for the classifier on the test set. (D) Performance, expressed as ROC AUC values, of the condensed biomarker signature obtained by the backward elimination strategy (solid line) as compared to that of 25-analyte signatures obtained by either i) 1000 random 25-marker signatures (open circles), ii) lowest p-values (dashed line), or iii) highest fold-change (dotted line). (E) Comparison of the ROC AUC value obtained for the condensed 25-analyte biomarker signature on the test set, when the sample annotation was correct (solid line) or permutated a 1000 times (open circles).

Figure 5:
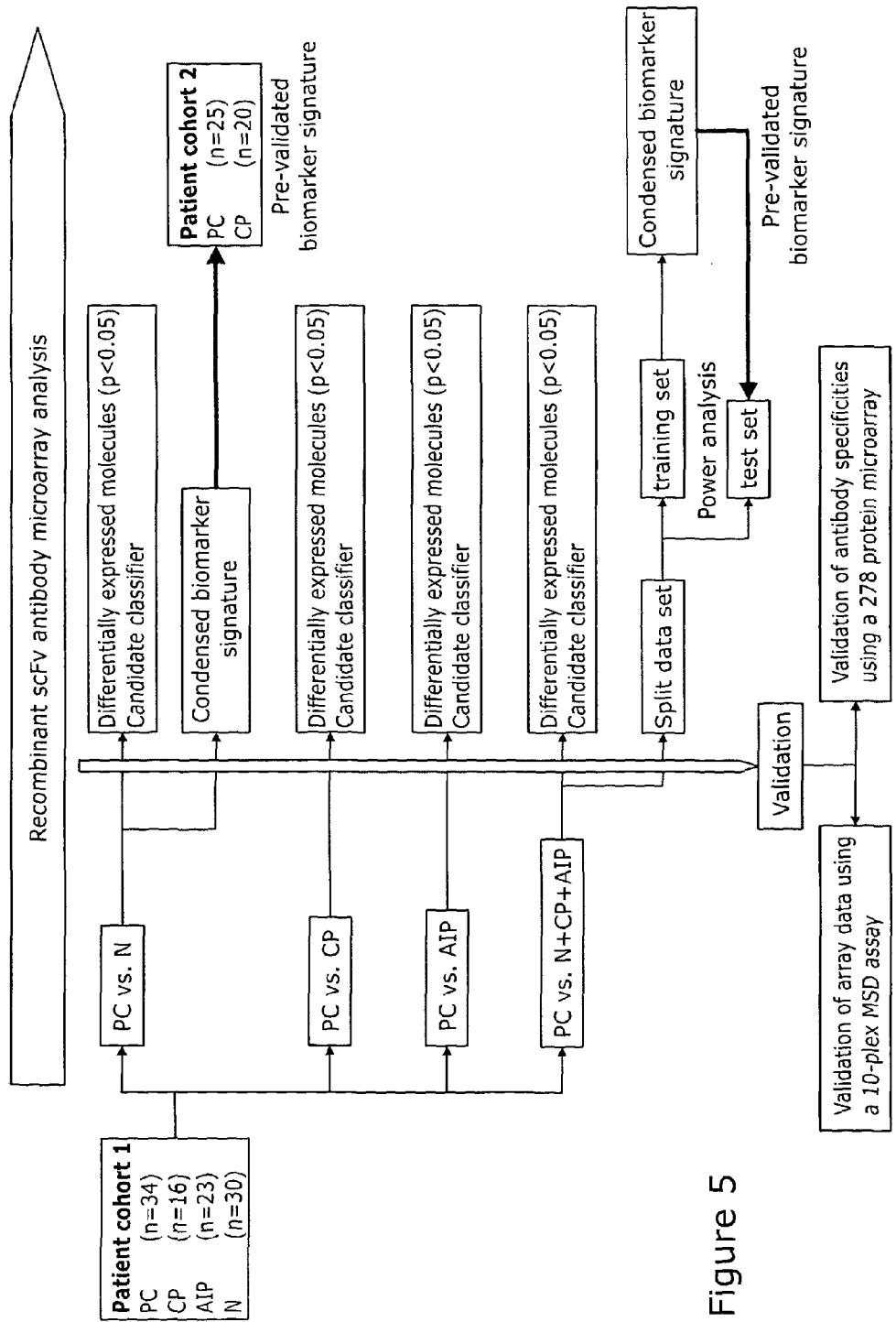

FIG. 5: Schematic outline of the antibody microarray strategy

Figure 6:
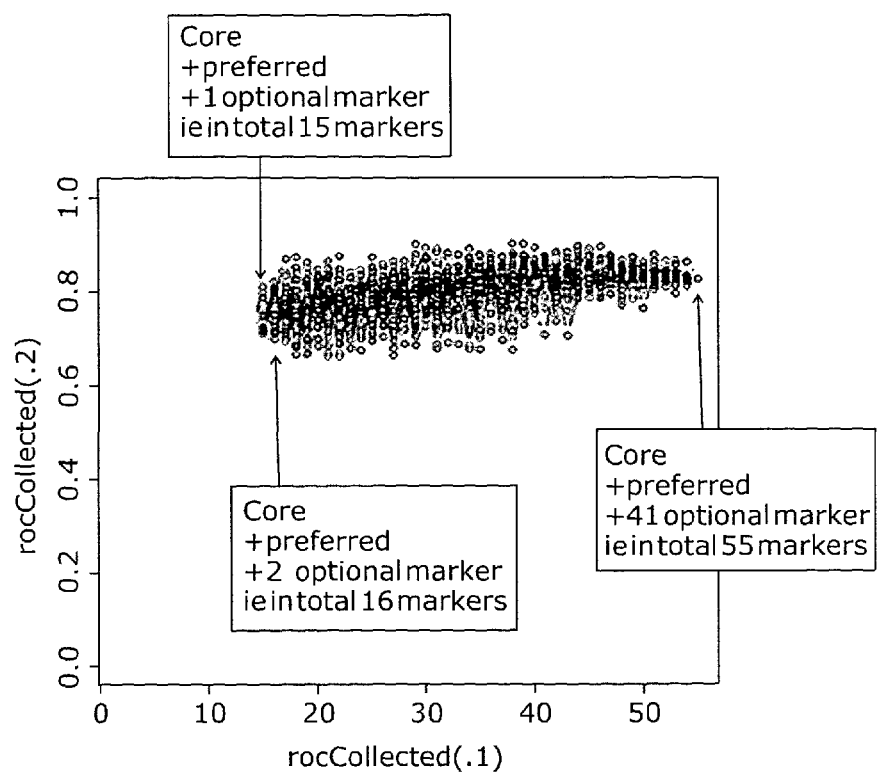

FIG. 6: ROC-AUC values for differentiation between (A) pancreatic cancer, and (B) normal, chronic pancreatitis, and/or acute inflammatory pancreatitis ROC-AUC values are shown for marker signatures having all of the Table IV(A) (i.e., core) and Table(B) (i.e., preferred) markers, and increasing numbers of Table(C) (i.e., optional) markers. The best ROC AUC value (0.90) is obtained for a 29 analyte signature, i.e., core markers+ preferred markers+15 optional markers. However, all marker combinations had substantial predictive power.

EXAMPLES

Materials and Methods

Serum Samples

Serum samples were collected at the time of diagnosis, i.e. prior to commencing any therapy, from two independent patient cohorts and stored at −80° C. In the first cohort, serum samples from 103 patients, diagnosed with pancreatic cancer (PaC) (n=34), chronic pancreatitis (ChP) (n=16), autoimmune pancreatitis (AIP) (n=23), or healthy individuals (N) (n=30) (no clinical symptoms) were screened. The patient demographics are described in Table 1. This cohort was randomly split and used as training set and test set. The second cohort, comprised of 45 patients, diagnosed with PaC (n=25), or N (n=20) (for patient demographics, see [14]), was used as an independent test set only, using antibody microarray data recently collected [14]. The size of the sample cohorts was limited by the availability of well-characterized serum samples collected at the time of diagnosis.

Antibody Microarray Analysis

The recombinant antibody microarray analysis was performed using previously in-house optimized protocols [12-15] (see below). Briefly, 121 human recombinant single-chain Fv (scFv) antibodies, targeting 57 mainly immunoregulatory analytes, were used as probes. The specificity, affinity (nM range), and on-chip functionality of the phage-display derived scFvs [16] was ensured by using i) stringent selection protocols [16], ii) multiple clones (<4) per target analyte, and iii) a scFv library microarray adapted by molecular design (REF). The planar antibody microarrays (array size; 160×8, <0.5 cm$^2$) were prepared by dispensing the antibodies and controls one-by-one (330 pL/drop) using a non-contact dispenser. The biotinylated serum samples were separately screened and specifically bound analytes were visualized by adding fluorescently labelled streptavidin using a confocal fluorescence scanner. Each individual array data point represents the mean value of four replicates. Chip-to-chip normalization was performed by using a semi-global normalization approach. In accordance to previous studies [12, 15, 17], the correlation coefficient for spot-to-spot reproducibility and array-to-array reproducibility was 0.99 and 0.94, respectively. Selected antibody specificities and microarray data were validated (Table II) using a 234 human protein array and a 10-plex cytokine sandwich antibody microarray, respectively. In addition, several antibody specificities have previously been validated using ELISA, protein arrays, blocking/spiking experiments, and/or mass spectrometry (Table II).

Microarray Data Analysis

The data analysis was performed in R (see below). Briefly, a support vector machine (SVM) was employed to classify the samples as belonging to one of two defined groups (e.g. cancer vs. healthy), using a linear kernel with the cost of constraints set to 1. No attempts were made to tune it in order to avoid the risk of over-fitting. The SVM was trained and tested using a leave-one-out (LOO) cross validation procedure. In two of the comparisons, this training part included the creation of an antibody sub-panel by selecting antibodies that, in the training set, displayed the highest discriminatory power. This selection of antibodies was made using either a direct or a cross-validated backward elimination strategy. Using this approach, condensed candidate biomarker signatures were identified, and subsequently evaluated on independent test sets.

Sensitivity and specificity values were calculated from the SVM decision values, using a threshold level of zero. A receiver operating characteristics (ROC) curve was constructed using the SVM decision values. The area under the curve (AUC) was calculated and used as a measure of prediction performance. Further, the Wilcoxon p-value and the fold change were calculated for each antibody. The candidate biomarker signatures were reported following the recommendations for tumour marker prognostic studies [18].

Serum Samples

After informed consent, serum samples were collected from two independent patient cohorts at the time of diagnosis, i.e. prior to initiation of therapy, and stored at −80° C. PC was verified with histology. Patient cohort 1 was composed of serum samples from 103 patients (Mannheim University Hospital, Germany), diagnosed with pancreatic ductal adenocarcinoma (PaC) (n=34), chronic pancreatitis (hCP) (n=16), autoimmune pancreatitis (AIP) (n=23), or healthy individuals (controls; N) (n=30) (no clinical symptoms). The patient demographics are described in Table 1. This cohort was also randomly split and used as training set (two thirds of the samples) and test set (one third). Patient cohort 2 was composed of 45 patients, diagnosed with PaC (n=25), or N (n=20) (Stockholm South General Hospital and Lund University Hospital, Sweden) (for patient demographics, see [39]), and was adopted using antibody microarray data as recently described [39]. A power analysis (see below) was performed in order to confirm that the size of the sample cohorts was sufficient to provide a statistical power >80%. The main experiments were performed on patient cohort 1, while cohort 2 was used as an independent data set for validation in one experiment (see FIG. 5).

Labelling of Serum Samples

The serum samples were labelled using previously optimized labelling protocols for serum proteomes [39-43]. Briefly, crude serum samples were thawed on ice and 30 µL aliquots were centrifuged (16 000× g for 20 min at 4° C.). Five µL of the supernatant was diluted 45 times in PBS, resulting in a protein concentration of approximately 2 mg/mL. Samples were labelled with EZ-link® Sulfo-NHS-LC-Biotin (Pierce, Rockford, Ill., USA) at a final concentration of 0.6 mM for 2 h on ice with gently vortexing every 20 min. Free biotin was removed by dialysis against PBS for 72 h at 4° C. using 3.5 kDa MW cut-off dialysis units (Thermo Scientific, Rockford, Ill., USA). The samples were aliquoted and stored at −20° C.

Production and Purification of scFv

In total, 121 human recombinant single-chain Fv (scFv) antibody fragments, targeting 57 mainly immunoregulatory biomolecules were selected from the n-CoDeR library [43] and kindly provided by BioInvent International AB, Lund, Sweden, or provided by Prof. Mats Ohlin (Lund University, Sweden) (5 clones against mucin-1). The specificity, affinity (nM range) and on-chip functionality of the phage-display derived scFv was ensured by using i) stringent selection protocols [43], ii) multiple clones (≤4) per target molecule, and iii) a scFv library microarray adapted by molecular design [44, 45]. The antibody fragments were produced in 100 mL *E. coil* cultures and purified from either expression supernatants or cell periplasm, using affinity chromatography on Ni-NTA agarose (Qiagen, Hilden, Germany). Bound molecules were eluted with 250 mM imidazole, extensively dialysed against PBS and stored at 4° C. until used for microarray fabrication. The antibody concentration was determined by measuring the absorbance at 280 nm (average 500 μg/mL, range 50-1840 μg/mL).

Fabrication and Processing of Antibody Microarrays

For the production of planar antibody microarrays, we used a set-up previously optimized and validated [39-43, 46]. Briefly, scFvs were arrayed onto balck polymer Maxisorb microarray slides (NUNC, Roskilde, Denmark) using a non-contact printer (BioChip Arrayer, PerkinElmer Life & Analytical Sciences, Wellesley, Mass., USA) by depositing approximately 330 pL drops, using piezo technology. Two drops were spotted in each position, allowing the first drop to dry out before the second drop was dispensed. In average, 5 fmol antibody (rang 1.5-25) was deposited per position. In order to ensure adequate statistics and to account for any local defects, each probe was printed in eight replicates. In total, 160 probes, including position markers and control scFvs were printed per slide, oriented in eight 20×8 subarrays. To assist grid alignment during quantification, a row of Alexa647 conjugated Streptavidin (Invitrogen, Carlsband, Calif., USA) (10 μg/mL) was spotted at selected positions. The arrays were blocked in 5% (w/v) fat-free milk powder (Semper AB, Sundbyberg, Sweden) in PBS over night.

The microarray slides were processed in a ProteinArray Workstation (PerkinElmer Life & Analytical Sciences) according to a previously described protocol [42]. Briefly, the arrays were washed with 0.5% (v/v) Tween-20 in PBS (PBS-T) for 4 min at 60 μL/min and then incubated with 75 μL biotinylated serum sample (diluted 1:2, resulting in a total serum dilution of 1:90) in 1% (w/v) fat-free milk powder and 1% (v/v) Tween-20 in PBS (PBS-MT), for 1 h with agitation every $15^{th}$ second. Next, the arrays were again washed with PBS-T and incubated with 1 μg/mL Alexa-647 conjugated streptavidin in PBS-MT, for 1h. Finally, the arrays were washed with PBS-T, dried under a stream of nitrogen gas and scanned with a confocal microarray scanner (PerkinElmer Life & Analytical Sciences) at 10 μm resolution, using four different scanner settings of PMT gain and laser power. The intensity of each spot was quantified in the ScanArray Express software v.4.0 (PerkinElmer Life & Analytical Sciences), using the fixed circle method. The local background was subtracted. To compensate for any possible local defects, the two highest and the two lowest replicates were automatically excluded and the mean value of the remaining four replicates was used. For antibodies displaying saturated signals, values from lower scanner settings were scaled and used instead. Chip-to-chip normalization was performed using a semi-global normalization approach previously described [39, 40, 42]. First, the CV for each probe over all samples was calculated and ranked. Second, 15% of the probes that displayed the lowest CV-values over all samples were identified and used to calculate a chip-to-chip normalisation factor for each array. The normalization factor $N_i$ was calculated by the formula $N_i=S_i$ 1 μ, where $S_i$ is the sum of the signal intensities for the antibodies used, averaged over all samples and μ is the sample average of $S_i$. The intensities were recalculated to log2 values prior to statistical analysis.

Validation of Antibody Specificity

The specificities of two selected scFvs (anti-IL-6 (2) and anti-IL-10 (1)) were tested using RayBio® 278 Human Protein Array G series (Norcross, GA, USA), according to protocol provided by the manufacturer. The scFvs were labelled with EZ-link® Sulfo-NHS-LC-Biotin (Pierce) for 2 h on ice at a 3.5 times molar excess of biotin. Unbound biotin was removed by 72 h dialysis against PBS. In total, 5 μg of antibody was added to each array. Binding was detected using 1 μg/mL Alexa647 conjugated Streptavidin (Invitrogen). PBS was added to one array as a negative control to check for unspecific binding of Streptavidin. The arrays were scanned and the signals from the negative control array were subtracted. In addition, several antibody specificities have previously been validated using well-characterized, standardized serum samples, and independent methods, such as mass spectrometry, ELISA, MSD, and CBA, as well as using spiking and blocking experiments (Table II).

Validation of Array Data

A human Th1/Th2 10-plex MSD (Meso Scale Discovery, Gaithersburg, Md., USA) assay was run in an attempt to validate the antibody microarray results. Each well of the MSD 96-plate had been pre-functionalized with antibodies against IFN-γ, IL-1β, IL-2, IL-4, IL-5, IL-8, IL-10, IL-12p70, IL-13 and TNF-α in spatially distinct electrode spots. A total of 34 serum samples (undiluted) were analyzed, including 11 PaC, 11 healthy, 9 ChP and 3 AIP samples (the low number of AIP samples was due to limited sample volumes in that subgroup). The assay was run according to the protocol provided by the manufacturer and the electrochemilluminiscence-based readout was performed in an MSD SECTOR® instrument.

Microarray Data Analysis

All statistics and data analysis was performed in R (http://www.r-project.org). Briefly, a support vector machine (SVM) was employed to classify the samples as belonging to one of two defined groups (e.g. cancer or healthy), using a linear kernel with the cost of constraints set to 1. No attempts were made to tune it in order to avoid the risk of over-fitting. The SVM was trained and tested using a leave-one-out (LOO) cross validation procedure [42]. In two of the comparisons, this training part included creating an antibody sub-panel by selecting antibodies that, in the training set, displayed the highest discriminatory power. This selection of antibodies was made using either a direct or a cross-validated backward elimination strategy. Using this approach, condensed candidate biomarker signatures were identified, and subsequently evaluated on independent test sets.

Sensitivity arid specificity values were calculated from the SVM decision values, using a threshold level of zero. A receiver operating characteristics (ROC) curve was constructed using the SVM decision values. The area under the curve (AUC) was calculated and used as a measure of prediction performance. Further, the Wilcoxon p-value and the fold change were calculated for each antibody. The candidate biomarker signatures were reported following the recommendations for tumour marker prognostic studies [47].

Biomarker Signatures Identification

A backward elimination procedure was used for identifying a biomarker signature for distinguishing PaC from healthy individuals. In this approach, one sample at the time was excluded from the dataset. The remaining samples were used for training the SVM by excluding one antibody at the time and performing the classification using the remaining antibodies. When all antibodies had been left out once, the least informative antibody was defined as the one that had been excluded when the smallest Kullback-Leibler (KL) error was obtained for the classification, and was eliminated from the dataset. The LOO procedure was iterated until only one antibody was left and the order by which the antibodies had been eliminated was recorded. The procedure was repeated by excluding a new sample and the iteration continued until all samples had been left out once. A list of the order in which the antibodies were eliminated was generated for each time a sample was excluded. In the end, all samples had been left out once and a consensus list was created where each antibody was assigned a score based on how long it had endured the elimination process, averaged over all iterations performed. Throughout the process, each left out sample was used to test the SVM models built for each new length of antibody subpanels, returning a decision value corresponding to the performance. Consequently, decision values for all samples for any given subpanel length were collected. The corresponding ROC areas were plotted against number of antibodies as a means to evaluate the strength of the data set and the elimination strategy. A condensed signature of 18 analytes was selected from the consensus list and an independent data set from antibody microarray analysis of 25 PaC and 20 N serum samples [39] was used as a test set for pre-validation of the candidate signature. The signature analytes were used in a SVM LOO cross validation procedure in the test set and the ability of the signature to distinguish PaC from N was illustrated in a ROC curve.

A second candidate biomarker signature was generated for classification of PaC among both N, ChP and AIP. First, the data was randomly divided into a training set (two thirds of the samples) and a test set (one third). A modified (even more stringent) backward elimination strategy was used. Instead of leaving out one sample at the time, the SVM was trained only once, using all samples in the training set. Consequently, one elimination list was generated from which a condensed panel of 25 analytes was selected and used to build the SVM in the training set. The model was applied onto the independent test set and a ROC curve was generated. Furthermore, a statistical power analysis was performed to estimate the number of patients required in the test set using the function "power.t.test" in R (decision values assumed normally distributed as suggested by Shapiro-Wilk testing). The observed decision values from the SVM analysis in the training set displayed a standard deviation of 2.87 and a delta value between the groups of 3.47 (difference between mean values). The alpha level (level of significance) was set to 0.05. In addition, the validity of this backward elimination procedure was tested by comparing the performance of the selected signature to 1000 randomly generated signatures of the same length and to signatures generated by selecting the antibodies of the lowest p-value and highest fold-change, respectively. Finally, the strength of the classifier and the data set was tested by comparing the performance of the signature in the test dataset to random data, by generating 1000 permutation of the sample annotations in the test data set.

Results

Classification of PaC vs. Healthy Controls

In order to identify serum biomarker signature associated with PaC, we performed differential serum protein expression profiling of PaC (n=34) vs. N (n=30), using the first patient cohort. A representative image of an antibody microarray is shown in FIG. 1A, illustrating that dynamic signal intensities, adequate spot morphology and low non-specific background binding were obtained. The results showed that 33 non-redundant protein analytes, including e.g. both Th1 and Th2 cytokines, were found to be differentially expressed (p<0.05), of which all, but the complement proteins C1q and Properdin, were up-regulated in PaC (FIG. 1B).

Figure 1D:
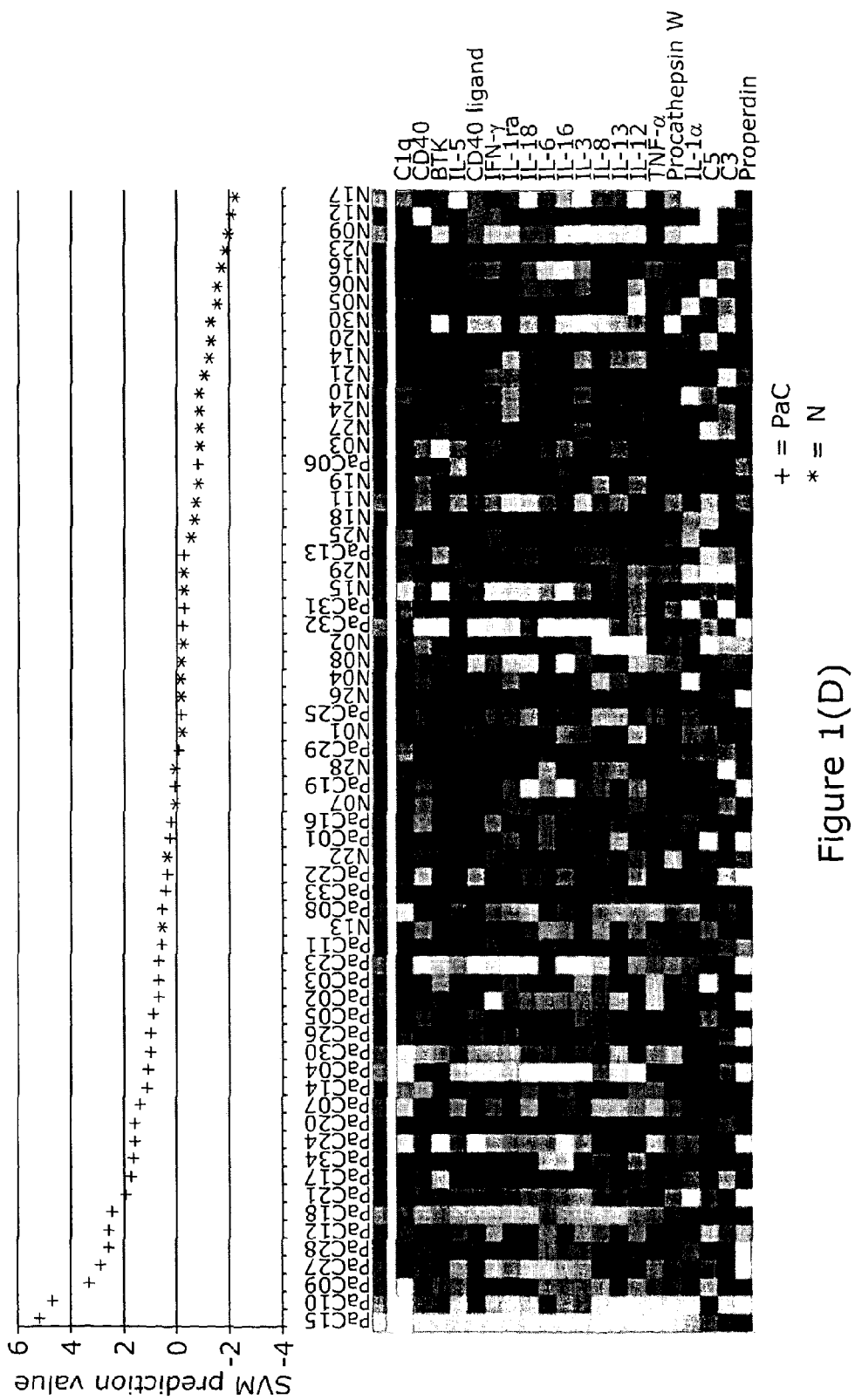

To investigate whether PaC and N could be differentiated, we ran a SVM LOO cross-validation, based on all antibodies, i.e. using unfiltered data. The data showed that the patient cohorts could be classified with a ROC AUC value of 0.94 (FIG. 10). In FIG. 1D, the samples are plotted by decreasing SVM decision value, and the relative expression pattern of the top 20 differentially expressed analytes (p<0.02) are shown in a heat map. By using a threshold of 0 (default value), the analysis showed that PaC vs. N could be classified with a sensitivity and specificity of 82% and 87%, respectively.

Figure 1E:
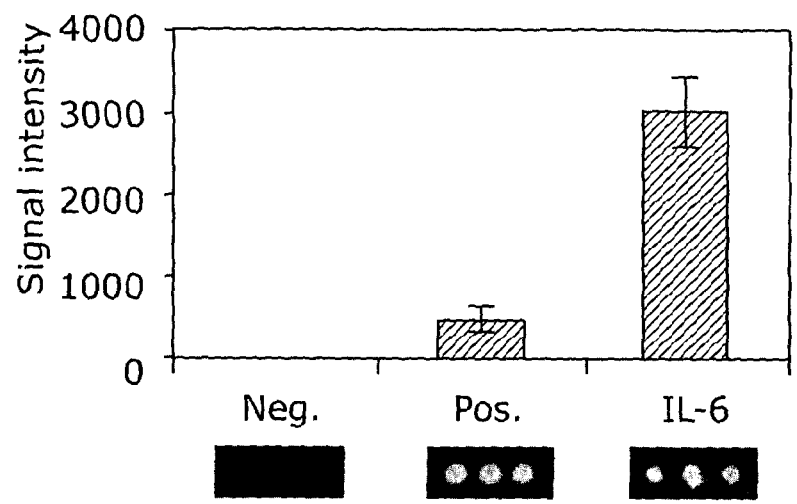
Figure 1F:
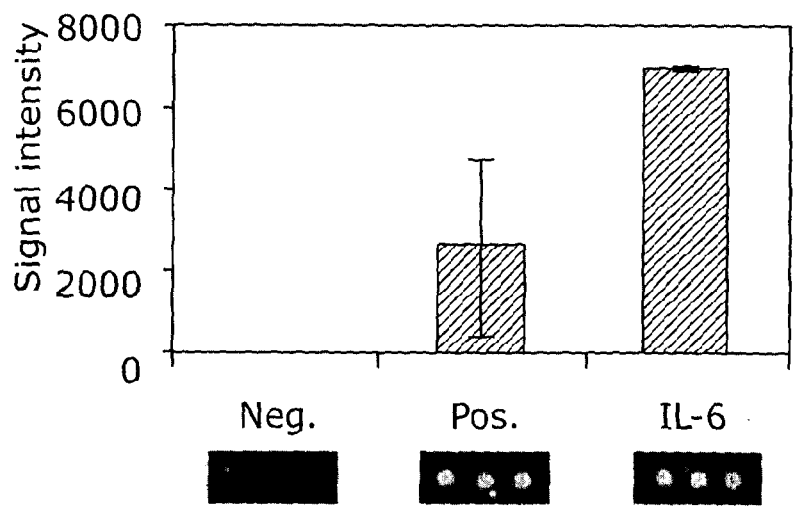

Next, a 278 human protein array was used for validation of selected antibody specificities (FIGS. 1E and 1F). To this end, scFv antibodies against one highly differentially expressed analyte, IL-6 (p=0.005), and one modest differentially expressed analyte, IL-10 (p=0.04), were selected. In both cases, the protein array analysis showed that the scFv antibody fragments bound specifically to their target protein.

Pre-Validation of Condensed Biomarker Signature for PaC vs. N Classification

In order to test the strength of the classification derived from the first patient cohort (n=64), we first condensed the total number of analytes down to the 18 non-redundant biomarkers contributing the most to the classification, by combining our LOO procedure with an iterative backward elimination strategy. In this process, the Kuliback-Leibler divergences error was minimized and used as guide for stepwise removal of the antibodies one-by-one. After each round, the SVM decision values were collected and the corresponding ROC curve and AUC value were calculated. In FIG. 2A, the AUC value is plotted against the number of remaining antibodies, indicating a high and stable classification even when only a few antibodies were included. The 18-analyte condensed candidate serum biomarker signature, composed of a variety of analytes, e.g. cytokines, complement proteins and enzymes, is shown in FIG. 2B. Next, we applied this 18-analyte classifier on a new independent test group, the second patient cohort (n=45) (FIG. 2C). The results showed that the classifier allowed a stratification of patients into PaC vs. N with a ROC AUC value of 0.95 (FIG. 2D), corresponding to a sensitivity of 88% and specificity of 85%. Hence, the data outlined the first pre-validated serum biomarker signature for PaC diagnosis.

Biomarker Signatures Differentiating PaC vs. Pancreatitis

Figure 3A:
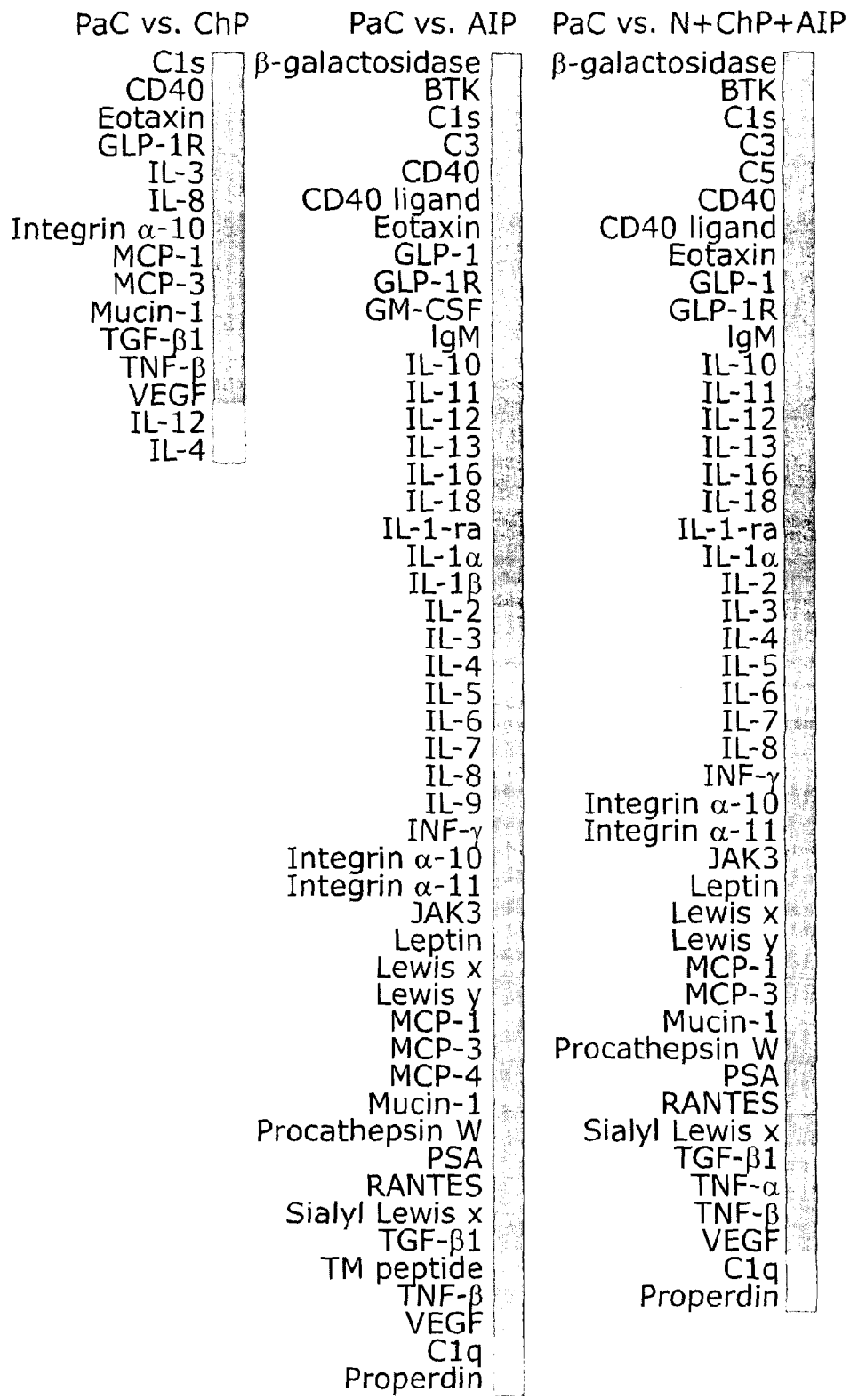

To test whether cancer could be differentiated from benign conditions in the pancreas, we compared the serum protein expression profile of PaC (n=34) with that of ChP (n=16) or AIP (n=23) using the first patient cohort. In the case of PaC vs. ChP, 15 non-redundant differentially expressed (p<0.05) serum analytes were pin-pointed, of which all but two (IL-4 and IL-12) were up-regulated in PaC (FIG. 3A). Based on unfiltered data, the results showed that PaC and ChP could be differentiated with a ROC AUC value of 0.86 (FIG. 3B), corresponding to a 97% sensitivity and 69% specificity. A total of 49 non-redundant serum analytes were found to be differentially expressed in PaC vs. AIP, with all except for C1q and Properdin, being up-regulated in PaC (FIG. 3A). Again, based on unfiltered data, the results showed that PaC vs. AIP could be classified with a ROC value of 0.99 (FIG. 3B), based on a sensitivity and specificity of 97% and 91%, respectively.

Figure 3B:
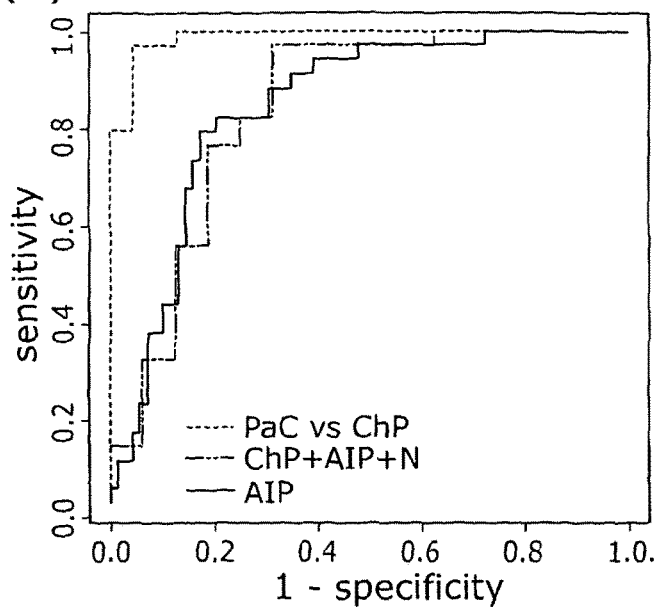

To better reflect the clinical reality, we then investigated whether differences could be deciphered between PaC and the combined, heterogeneous patient group of ChP+AIP+N, using the first patient cohort (n=103). The results showed that 47 non-redundant serum proteins were differentially expressed (p<0.05) (FIG. 3A). A majority of the analytes (45 of 47) were found to be up-regulated in PaC, including a wide range of proteins. Based on unfiltered data, the results showed that PaC could be distinguished from this heterogeneous patient group with a ROC AUC value of 0.85 (FIG. 3B).

Figure 3C:
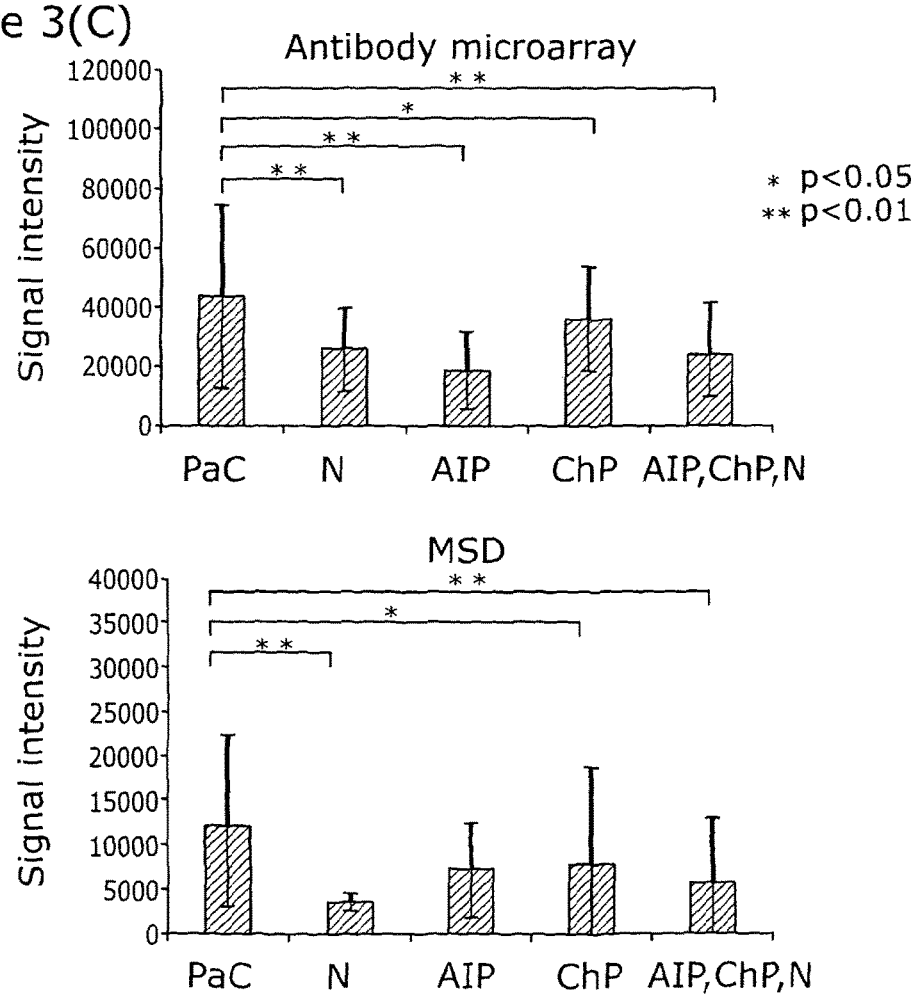

In an attempt to validate the array data, an independent 10-plex cytokine sandwich antibody microarray (MSD) was applied (FIG. 3C). However, only 1 of 10 targeted serum analytes, IL-8, was above the lower limit of detection of the MSD assay in a majority of the samples. Still, the observed up-regulation of IL-8 in PaC vs. N, ChP, AIP and combined cohort thereof was statistically confirmed (p<0.05) by the MSD assay in all cases, except for PaC vs. AIP (p=0.29).

Refined Biomarker Signature for PaC Diagnosis

Figure 4C:
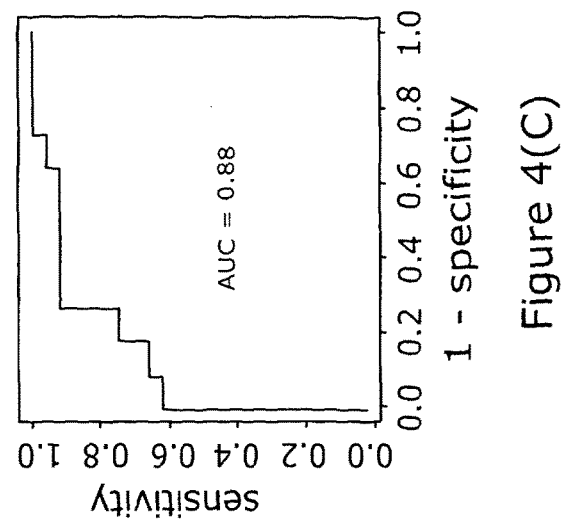
Figure 4B:
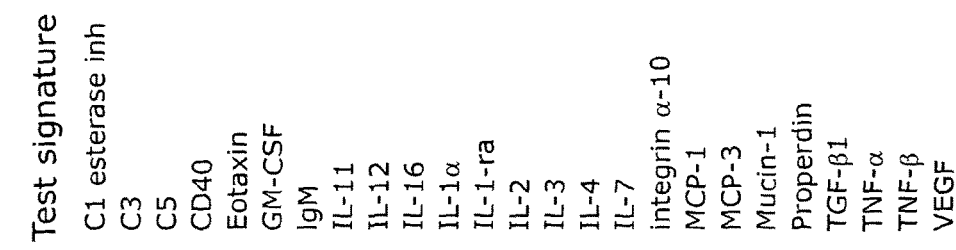
Figure 4A:
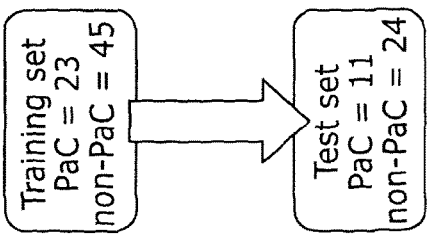

To test the strength of the classification of the entire first patient cohort, including PaC, N, ChP and AIP (n=103), we split the cohort into a training set (two thirds) and test set (one third) (FIG. 4A). Next, a condensed serum biomarker signature composed of the 25 non-redundant analytes contributing the most to the classification in the training set was deciphered by using a direct, iterative backward elimination strategy. The 25-analyte condensed biomarker signature, composed of e.g. cytokines and complement proteins, is shown in FIG. 4B. Next, we applied this 25-analyte classifier on the independent test set (FIG. 4C). The data showed that PaC could be pinpointed with a ROC AUC value of 0.88 (FIG. 4C), outlining a sensitivity and specificity of 73% and 75%, respectively.

Figure 4D:
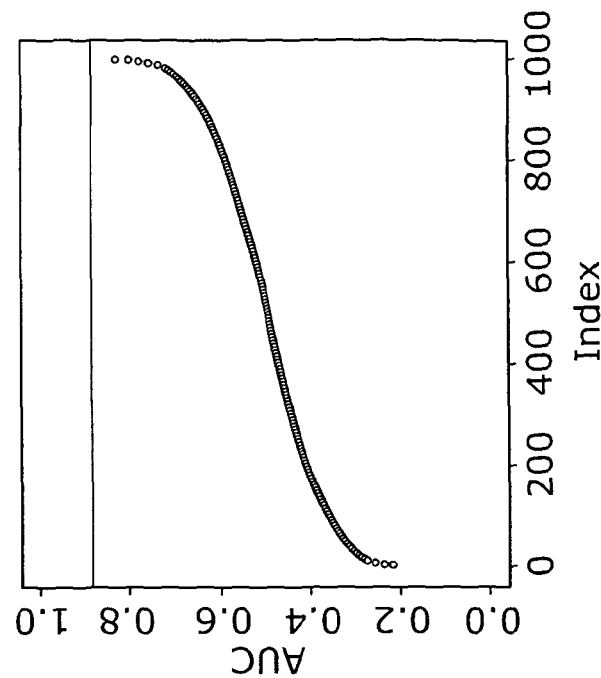
Figure 4E:
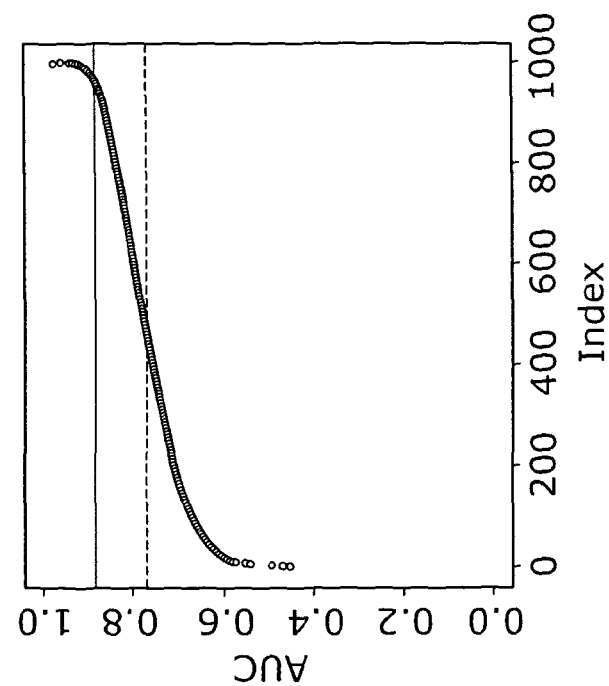

To further challenge the classifier, we statistically evaluated its discriminatory power. Firstly, 1000 random signatures of the same length (25 antibodies) were generated in the training set and applied to the test set. The results showed that the AUC values for the random signatures were lower than that of the classifier biomarker signature (AUC=0.88) in 95% of the cases (FIG. 4D). In addition, the AUC values for the corresponding 25-analyte signature selected based on either lowest p-values (AUC=0.77) or highest fold-changes (AUC=0.78) were significantly lower than that of the classifier signature. Hence, the data further indicated the discriminatory power of the classifier, and the applicability of the backward elimination strategy for defining a condensed, high-performing signature. Secondly, the sample annotation of the test set was permutated 1000 times in order to compare the specific classification to random classification of the same number of samples. The results showed that a significantly higher AUC value (0.88 vs. 0.19-0.86, median value of 0.5) was obtained when the correct sample annotation was used than when the random annotation was applied, further demonstrating the strength of the classification.

Discussion

In this study, we have applied affinity proteomics in order to harness the diagnostic power of the immune system to target PaC. We based our approach on the notion that the immune system is exquisitely sensitive to alterations in an individual's state of health, resulting from disease, registering these changes through fluctuations in the levels of, in particular, immunoregulatory analytes. To this end, we designed our antibody microarray to target predominantly these kinds of key regulatory serum analytes. The data showed that PaC-associated candidate biomarkers signatures displaying high diagnostic power could be de-convoluted. In a similar fashion, this affinity proteomic approach has recently allowed the identification of several serological biomarker signatures distinguishing other cancer indications and healthy controls [14-15, 17, 19], further demonstrating the strength of the platform.

We showed for the first time that serum stored information enabling us to discriminate between not only well-defined patient cohorts of PaC vs. controls and PaC vs. pancreatitis, but also between PaC vs. the combined cohort of controls and pancreatitis patients with high confidence. This latter finding was in particular critical, since the candidate biomarker signatures must perform well also in clinical settings where heterogeneous patients groups will be screened.

The clinical impact of a high-performing PaC classifier would be high as no validated serological discriminator is yet in place [2, 7-9, 20-21]. While waiting for a golden classifier to be established, CA-19-9 remains the most useful molecular marker for PaC diagnosis [2, 8-10]. Notably, our data showed a significantly higher median sensitivity (88%) and specificity (85%) for PaC diagnosis than what have been consistently observed for CA-19-9 [2. 9-11], outlining a significant clinically added value. Further, we have recently modelled the impact of new diagnostic possibilities on cost, survival, and quality of life for risk patients, and showed that affinity proteomics had great prospects for becoming a cost-effective tool in screening for PaC (Bolin et al, ms in prep.).

The classifier will perform at its best if early diagnosis, when the tumour is still small and operable, could be performed [2, 9].

In the quest for cancer biomarkers, systemic inflammation is frequently highlighted as a potential confounding factor [23], since cancer development and inflammation has been linked. In early works based on affinity proteomics, the results also often showed that general disease (inflammatory) signatures rather than cancer-specific fingerprints were delineated [24-26]. Notably, we showed here that PaC and pancreatitis could be discriminated with high confidence. Furthermore, the observed signature(s) showed significant differences, i.e. only small overlaps, with those observed for other various inflammatory conditions refs [19, 27] (Carlsson et al., ms in prep.) and other cancers [14-15, 17, 19], further supporting the notion that PaC-specific signatures were deciphered.

The serum immunosignatures could be considered as snapshots of the immune system's activity in a patient at the time of the test. These fingerprints will reflect a combination of direct and indirect (systemic) effects in response to the cancer. Focusing on the cytokine expression profiles, previous reports have shown that pancreatic cancer cell lines expressed a set of cytokines found to be over expressed also in this study, including e.g. IL-6, IL-8, IL-10, IL-12, IL-13, IL-18, and TGF-β1. Several of these and other cytokines (e.g. VEGF and IL-7) have also been found to be overexpressed in PaC tumour tissue and/or serum/plasma [29-33] further supporting our observations. Although cytokines play a pivotal role in the immune system, interpreting these intricate expression patterns in a biological context is demanding since many of these analytes display pleiotropic functions and PaC is characterized by peculiar cytokine expression patterns [29]. While the expression of e.g. IFN-γ could signal an attempted anti-tumour immune response [29], the immunological environment of PaC has often been found to be in an immunosuppressive site, as illustrated by the concomitant expression of anti-inflammatory cytokines (e.g. TGF-β and IL-10), and potentially inactive proinflammatory cytokines (e.g. IL-12 and IL-18) [29]. A cellular immunosuppression is a striking biological feature of PaC observed in many patients [34]. While Th2 skewed responses have been reported, the Th1/Th2 balance indicated here has also been observed [29, 31, 35]. The cytokine expression pattern has also been found to reflect other parameters, such as survival [14, 29]. Looking at some of the non-cytokine markers, several complements proteins, such as C3, which has been suggested to function in immune surveillance against tumours [36-37], and the carbohydrate antigen Lewis x have also previously been found to be associated with PaC [38].

Taken together, we have addressed a clinical need and demonstrated that immunosignaturing was a powerful approach for deciphering the first pre-validated serological biomarker signatures for PaC diagnosis. This was achieved through a high-performing platform, well-controlled samples and stringent bioinformatic and validation approaches. The potential of the predictor signature will be further validated in follow-up studies, in which independent sample cohorts will be profiled. In the end, these findings will provide novel opportunities for improved PaC diagnosis and thereby enhanced prognosis and clinical management of PaC.

References

1. Hidalgo, M., *Pancreatic cancer.* N Engl J Med, 2010. 362(17): p. 1605-17.

2. Chu, D., W. Kohlmann, and D. G. Adler, *Identification and screening of individuals at increased risk for pancreatic cancer with emphasis on known environmental and genetic factors and hereditary syndromes.* JOP, 2010. 11(3): p. 203-12.

3. Jemal A, S. R., Ward E, Hao Y, Xu J, Thun M J., *Cancer statistics,* 2009. CA Cancer J Clin, 2009. 59(4).

4. Pannala, R., et al., *New-onset diabetes: a potential clue to the early diagnosis of pancreatic cancer.* Lancet Oncol, 2009. 10(1): p. 88-95.

5. Warshaw. A. L. and C. Fernandez-del Castillo, *Pancreatic carcinoma.* N Engl J Med, 1992. 326(7): p. 455-65.

6. Galasso, D., A. Carnuccio, and A. Larghi, *Pancreatic cancer: diagnosis and endoscopic staging.* Eur Rev Med Pharmacol Sci. 2010. 14(4): p. 375-85.

7. Chen, R., et al., *Proteomics studies of pancreatic cancer.* Proteomics Clin Appl, 2007. 1(12): p. 1582-1591

8. Duffy, M. J., et al., *Tumor markers in pancreatic cancer: a European Group on Tumor Markers (EGTM) status report.* Ann Oncol, 2010. 21(3): p. 441-7.

9. Fry L C, M. K., Malfertheiner P., *Molecular markers of pancreatic cancer: development and clinical relevance.* Langenbecks Arch Surg., 2008. 393(6).

10. Koopmann J, R. C., Zhang Z, Canto M I, Brown D A, Hunter M, Yeo C, Chan D W, Breit S N, Goggins M., *Serum markers in patients with resectable pancreatic adenocarcinoma: macrophage inhibitory cytokine 1 versus CA19-9.* Clin Cancer Res., 2006. 15(12).

11. Boeck S, S. P., Holdenrieder S, Wilkowski R, Heinemann V., *Prognostic and therapeutic significance of carbohydrate antigen 19-9 as tumor marker in patients with pancreatic cancer.* Oncology, 2006. 70(4).

12. Ingvarsson J, L. A., Sjoholm A G, Truedsson L, Jansson B, Borrebaeck C A, Wingren C., *Design of recombinant antibody microarrays for serum protein profiling: targeting of complement proteins.* J Proteome Res, 2007. 6(9).

13. Wingren C, I. J., Dexlin L, Szul D, Borrebaeck C A., *Design of recombinant antibody microarrays for complex proteome analysis: choice of sample labeling-tag and solid support.* Proteomics, 2007. 7(17).

14. Ingvarsson J, W. C., Carlsson A, Ellmark P, Wahren B, Engstrom G, Harmenberg U, Krogh M, Peterson C, Borrebaeck C A., *Detection of pancreatic cancer using antibody microarray-based serum protein profiling.* Proteomics, 2008. 8(11).

15. Carlsson, A., et al., *Plasma proteome profiling reveals biomarker patterns associated with prognosis and therapy selection in glioblastoma multiforme patients.* Proteomics Clinical Applications, 2010. 4(6-7): p. 591-602.

16. Söderlind E, S. L., Jirholt P, Kobayashi N, Alexeiva V, Aberg A M, Nilsson A, Jansson B, Ohlin M, Wingren C, Danielsson L, Carlsson R, Borrebaeck C A., *Recombining germline-derived CDR sequences for creating diverse single-framework antibody libraries.* Nat Biotechnol., 2000. 18(8).

17. Carlsson A, W. C., Ingvarsson J, Ellmark P, Baldertorp B, Fernö M, Olsson H, Borrebaeck C A., *Serum proteome profiling of metastatic breast cancer using recombinant antibody microarrays.* Eur J Cancer, 2008. 44(3).

18. McShane, L. M., et al., *REporting recommendations for tumor MARKer prognostic studies (REMARK).* Nat Clin Pract Oncol, 2005. 2(8): p. 416-22.

19. Ellmark P, I. J., Carlsson A, Lundin B S. Wingren C, Borrebaeck C A., *Identification of protein expression signatures associated with Helicobacter pylori infection and gastric adenocarcinoma using recombinant antibody microarrays.* Mol Cell Proteomics., 2006. 5(9).

20. Garcea, G., et al., *Molecular prognostic markers in pancreatic cancer: a systematic review.* Eur J Cancer, 2005. 41(15): p. 2213-36.

21. Rustgi, A. K., *Pancreatic cancer: novel approaches to diagnosis and therapy.* Gastroenterology, 2005. 129(4): p. 1344-7.

22. Biankin, A. V., et al., *Molecular pathogenesis of precursor lesions of pancreatic ductal adenocarcinoma.* Pathology, 2003. 35(1): p. 14-24.

23. Chechlinska, M., M. Kowalewska, and R. Nowak, *Systemic inflammation as a confounding factor in cancer biomarker discovery and validation.* Nat Rev Cancer. 2010. 10(1): p. 2-3.

24. Orchekowski, R., et al., *Antibody microarray profiling reveals individual and combined serum proteins associated with pancreatic cancer.* Cancer Res, 2005. 65(23): p. 11193-202.

25. Gao, W. M., et al., *Distinctive serum protein profiles involving abundant proteins in lung cancer patients based upon antibody microarray analysis.* BMC Cancer, 2005. 5: p. 110.

26. Miller, J. C., et al., *Antibody microarray profiling of human prostate cancer sera: antibody screening and identification of potential biomarkers.* Proteomics, 2003. 3(1): p. 56-63.

27. Dexlin-Mellby, L., et al., *Tissue proteomic profiling of preeclamptic placenta tissue using recombinant antibody microarrays.* Proteomics—Clinical Applications, 2010. 4(10-11): p. 794-807.

28. Bellone, G., et al., *Cytokine expression profile in human pancreatic carcinoma cells and in surgical specimens: implications for survival.* Cancer Immunol Immunother, 2006. 55(6): p. 684-98.

29. Bellone G, S. C., Mauri F A, Tonel E, Carbone A, Buffolino A, Dughera L, Robecchi A, Pirisi M, Emanuelli G., *Cytokine expression profile in human pancreatic carcinoma cells and in surgical specimens: implications for survival.* Cancer Immunol Immunother. , 2006. 55(6).

30. Chang S T, Z. J., Horecka J, Kunz P L, Ford J M, Fisher G A, Le Q T, Chang D T, Ji H, Koong A C., *Identification of a biomarker panel using a multiplexed*

*proximity ligation assay improves accuracy of pancreatic cancer diagnosis.* J Transl Med., 2009. 7(105).

31. Poch B, L. E., Ramadani M, Gansauge S, Beger H G, Gansauge F., *Systemic immune dysfunction in pancreatic cancer patients.* Langenbecks Arch Surg., 2007. 392(3).

32. Wigmore S J, F. K., Sangster K, Maingay J P, Garden O J, Ross J A., *Cytokine regulation of constitutive production of interleukin-8 and-6 by human pancreatic cancer cell lines and serum cytokine concentrations in patients with pancreatic cancer.* Int J Oncol., 2002. 21(4).

33. Frick V O, R. C., Wagner M, Graeber S, Grimm H, Kopp B, Rau B M, Schilling M K., *Enhanced ENA-78 and IL-8 expression in patients with malignant pancreatic diseases.* Pancreatology., 2008. 8(4-5).

34. Ungefroren, H., et al., *Immunological escape mechanisms in pancreatic carcinoma.* Ann N Y Acad Sci, 1999. 880: p. 243-51.

35. Schmitz-Winnenthal F H, V. C., Z'graggen K, Galindo L, Nummer D, Ziouta Y, Bucur M, Weitz J, Schirrmacher V, Büchler M W, Beckhove P., *High frequencies of functional tumor-reactive T cells in bone marrow and blood of pancreatic cancer patients.* Cancer Res., 2005. 65(21).

36. Chen R, P. S., Cooke K, Moyes K W, Bronner M P, Goodlett D R, Aebersold R, Brentnall T A., *Comparison of pancreas juice proteins from cancer versus pancreatitis using quantitative proteomic analysis.* Pancreas, 2007. 34(1).

37. Yu K H, R. A., Blair I A., *Characterization of proteins in human pancreatic cancer serum using differential gel electrophoresis and tandem mass spectrometry.* J Proteome Res., 2005. 4(5).

38. Nakano M, N. T., Ito T, Kitada T, Hijioka T, Kasahara A, Tajiri M, Wada Y, Taniguchi N, Miyoshi E., *Site-specific analysis of N-glycans on haptoglobin in sera of patients with pancreatic cancer: a novel approach for the development of tumor markers.* Int J Cancer., 2008. 122(10).

39. Ingvarsson J, Wingren C, Carlsson A, et al. Detection of pancreatic cancer using antibody microarray-based serum protein profiling. Proteomics 2008;8.

40. Carlsson A, Wingren C, Ingvarsson J, et al. Serum proteome profiling of metastatic breast cancer using recombinant antibody microarrays. Eur J Cancer 2008;44: 472-80.

41. Wingren C, Ingvarsson J, Dexlin L, Szul D, Borrebaeck C A K. Design of recombinant antibody microarrays for complex proteome analysis: choice of sample labeling-tag and solid support. Proteomics 2007;7:3055-65.

42. Carlsson A, Persson O, Ingvarsson J, et al. Plasma proteome profiling reveals biomarker patterns associated with prognosis and therapy selection in glioblastoma multiforme patients. Proteomics Clin Appl 2010;4:1-12.

43. Söderlind E, Strandberg L, Jirholt P, et al. Recombining germline-derived CDR sequences for creating diverse single-framework antibody libraries. Nat Biotechnol 2000; 18:852-6.

44. Borrebaeck C A K, Wingren C. Design of high-density antibody microarrays for disease proteomics: key technological issues. J Proteomics 2009;72:928-35.

45. Borrebaeck C A K, Wingren C. High-throughput proteomics using antibody microarrays: an update. Expert Rev Mol Diagn 2007;7: 673-86.

46. Ellmark P; ingvarsson J, Carlsson A, Lundin B S, Wingren C, Borrebaeck C A K. Identification of protein expression signatures associated with Helicobacter pylori infection and gastric adenocarcinoma using recombinant antibody microarrays. Mol Cell Proteomics 2006;5:1638-46.

47. McShane L M, Altman D G, Sauerbrei W, Taube S E, Gion M, Clark G M. REporting recommendations for tumor MARKer prognostic studies (REMARK). Nat Clin Pract Oncol 2005;2:416-22.

TABLE I

Patient demographics of the first patient cohort

| Class | No. of patients | Gender (M/F/unknown) | Mean (SD) | Age Range |
|---|---|---|---|---|
| PaC | 34 | 18/12/4 | 65.0 (10.4) | 42-93 |
| N | 30 | 15/15/0 | 33.2 (8.6) | 24-53 |
| ChP | 16 | 12/4/0 | 48.8 (14.2) | 32-73 |
| AIP | 23 | 11/11/1 | 42.4 (18.3) | 14-74 |
| All | 103 | 56/42/5 | 48.2 (18.1) | 14-93 |

TABLE II

Summary of serum biomarkers analyzed by the antibody microarrays

| Antigen (no. of clones) | Antigen (no. of clones) |
|---|---|
| Angiomotin (2) | IL-2 (3) |
| β-galactosidase (1) | IL-3 (3) |
| Bruton tyrosine kinase | IL-4 (4)** |
| BTK (1) | IL-5 (3)** |
| C1 Esterase inhibitor (1) | IL-6 (4)*/** |
| | IL-7 (2) |
| C1q (1)** | IL-8 (3)** |
| C1s (1) | IL-9 (3) |
| C3 (2)** | Integrin α10 (1) |
| C4 (1)** | Integrin α11 (1) |
| C5 (2)** | Leptin (1) |
| CD40 (4) | Lewis x (2) |
| CD40 ligand (1) | Lewis y (1) |
| CT-17 (control) (1) | MCP-1 (3)** |
| Digoxin (control) (1) | MCP-3 (1) |
| Eotaxin (3) | MCP-4 (2) |
| Factor B (1)** | Mucin-1 (6) |
| GLP-1 (1) | Procathepsin W (1) |
| GLP-1 R (1) | Properdin (1)** |
| GM-CSF (3) | PSA (1) |
| IFN-γ (2) | RANTES (2) |
| IgM (1) | Sialyl Lewis x (1) |
| IL-10 (3)* | TGF-β1 (3) |
| IL-11 (3) | TM peptide (1) |
| IL-12 (4)** | TNF-α (2) |
| IL-13 (2)** | TNF-β (4)** |
| IL-16 (2) | Tyrosine protein kinase |
| IL-18 (3) | JAK3 (1) |
| IL-1α (3)** | VEGF (4)** |
| IL-1β (3) | |
| IL-1-ra (3) | |

*Antibody specificity determined by protein array.
**Antibody specificity previously validated by ELISA, protein array, blocking/spiking experiments, and/or mass spectrometry.

TABLE III

Pancreatic Cancer Diagnostic Biomarkers

| Biomarker name | Exemplary sequences |
|---|---|
| Interleukin-7 (IL-7) | AK226000, AB102893, AB102885, P13232 |
| Integrin α-10 | Hs158237; 075578 |
| B-galactosidase | P16278 |
| Bruton's tyrosine kinase (BTK) | Q06187 |

TABLE III-continued

Pancreatic Cancer Diagnostic Biomarkers

| Biomarker name | Exemplary sequences |
|---|---|
| Complement protein C1q (C1q) | IPR001073, PR00007 |
| Complement protein C1s (C1s) | P09871 |
| B cell receptor μ chain (IgM) | e.g. P01871 (not complete protein); isotype-specific for IgM on Ramos B cells[1) |
| Interleukin-9 (IL-9) | P15248 |
| Integrin α-11 | Q9UKX5 |
| Janus kinase 3 protein tyrosine kinase (JAK3) | P52333 |
| Procathepsin W | P56202 |
| Properdin | P27918 |
| TM peptide (10TM protein) | NA - see above |
| Tumour necrosis factor-α (TNF-α) | P01375 |
| Angiomotin | AAG01851; Q4VCS5 |
| Complement-1 esterase inhibitor (C1-INH) | P05155 |
| Complement protein C3 (C3) | BC150179, BC150200; P01024 |
| Complement protein C4 (C4) | BC151204, BC146673, AY379959, AL645922, AY379927, AY379926, AY379925 |
| Complement protein C5 (C5) | BC113738, BC113740, DQ400449, AB209031, P01031 |
| CD40 | Q6P2H9 |
| Eotaxin | P51671 |
| Complement Factor B (Factor B) | P00751 |
| Glucagon-like peptide-1 (GLP-1) | |
| Glucagon-like peptide-1 receptor (GLP-1 R) | P43220 |
| Granulocyte-macrophage colony-stimulating factor (GM-CSF) | P04141 |
| Interleukin-10 (IL-10) | P22301 |
| Interleukin-11 (IL-11) | P20809 |
| Interleukin-12 (IL-12) | O60595 |
| Interleukin-13 (IL-13) | P35225 |
| Interleukin-18 (IL-18) | Q14116 |
| Interleukin-1α (IL-1α) | P01583 |
| Interleukin-1β (IL-1β) | P01584 |
| Interleukin-2 (IL-2) | P60568 |
| Interleukin-3 (IL-3) | P08700 |
| Interleukin-4 (IL-4) | P05112 |
| Interleukin-5 (IL-5) | BC066282, CH471062, P05113 |
| Interleukin-6 (IL-6) | P05231 |
| Interleukin-8 (IL-8) | CR623827, CR623683, DQ893727, DQ890564, P10145 |
| Interferon-γ (INF-γ) | P01579 |
| Leptin | P41159 |
| Lewis X/CD15 | Carbohydrate structure (not applicable) |
| Lewis y | Carbohydrate structure (not applicable) |
| Monocyte chemotactic protein-1 (MCP-1) | P13500 |
| Mucin-1 | P15941 |
| Prostate specific antigen (PSA) | P07288 |
| RANTES | P13501 |
| Sialyl Lewis x | Carbohydrate structure (not applicable) |
| Transforming growth factor-1 (TGF-b1) | P01137 |
| Tumour necrosis factor-β (TNF-β) | P01374 |
| Vascular endothelial growth factor (VEGF) | P15692, P49765, P49767, =O43915 |
| CD40 ligand | P29965 |
| Interleukin-16 (IL-16) | Q05BE6, Q8IUU6, B5TY35 |
| Interleukin-1ra (IL-1ra) | P18510 |
| Monocyte chemotactic protein-3 (MCP-3) | BC112258, BC112260, BC092436, BC070240 |
| Monocyte chemotactic protein-4 (MCP-4) | Q99616 |

TABLE IV

Pancreatic Cancer Diagnostic Biomarkers
Biomarker name (A) Core biomarkers

Interleukin-7 (IL-7)
Integrin α-10

(B) Preferred biomarkers

B-galactosidase
Bruton's tyrosine kinase (BTK)
Complement protein C1q (C1q)
Complement protein C1s (C1s)
B cell receptor μ chain (IgM)
Interleukin-9 (IL-9)
Integrin α-11
Janus kinase 3 protein tyrosine kinase (JAK3)
Procathepsin W
Properdin
TM peptide
Tumour necrosis factor-α (TNF-α)

(C) Optional additional biomarkers

Angiomotin
Complement-1 esterase inhibitor (C1-INH)
Complement protein C3 (C3)
Complement protein C4 (C4)
Complement protein C5 (C5)
CD40
Eotaxin
Complement Factor B (Factor B)
Glucagon-like peptide-1 (GLP-1)
Glucagon-like peptide-1 receptor (GLP-1 R)
Granulocyte-macrophage colony-stimulating factor (GM-CSF)
Interleukin-10 (IL-10)
Interleukin-11 (IL-11)
Interleukin-12 (IL-12)
Interleukin-13 (IL-13)
Interleukin-18 (IL-18)
Interleukin-1α (IL-1α)
Interleukin-1β (IL-1β)
Interleukin-2 (IL-2)
Interleukin-3 (IL-3)
Interleukin-4 (IL-4)
Interleukin-5 (IL-5)
Interleukin-6 (IL-6)
Interleukin-8 (IL-8)
Interferon-γ (IFN-γ)
Leptin
Lewis X/CD15
Lewis y
Monocyte chemotactic protein-1 (MCP-1)
Mucin-1
Prostate specific antigen (PSA)
Rantes
Sialyl Lewis x
Transformign growth factor-1 (TGF-b1)
Tumour necrosis factor-β (TNF-β)
Vascular endothelial growth factor (VEGF)
CD40 ligand
Interleukin-16 (IL-16)
Interleukin-1ra (IL-1ra)
Monocyte chemotactic protein-3 (MCP-3)
Monocyte chemotactic protein-4 (MCP-4)

TABLE V

Pancreatic Cancer Diagnostic Biomarker Subsets

| Biomarker name | PaC vs N P value | PaC vs N Backward | PaC vs N + Chp + AIP P value | PaC vs N + Chp + AIP backward | PaC vs ChP P value | PaC vs AIP P value |
|---|---|---|---|---|---|---|
| A | | | | | | |
| CD40 | X | | X | X | X | X |
| Interleukin-12 (IL-12) | X | X | X | X | X | X |
| Interleukin-3 (IL-3) | X | X | X | X | X | X |
| Interleukin-4 (IL-4) | | X | X | X | X | X |
| Interleukin-8 (IL-8) | X | | X | | X | X |
| Monocyte chemotactic protein-1 (MCP-1) | | X | X | X | X | X |
| Mucin-1 | | X | X | X | X | X |
| Transforming growth factor, beta-1 (TGF-b1) | X | X | X | X | X | X |
| Tumour necrosis factor-β (TNF-β) | | X | X | X | X | X |
| Vascular endothelial growth factor (VEGF) | X | X | X | X | X | X |
| B | | | | | | |
| B-galactosidase | X | | X | | | X |
| Bruton's tyrosine kinase (BTK) | X | X | X | | | X |
| CD40 ligand | X | X | X | | | X |
| Complement protein C1q (C1q) | X | | X | | | X |
| Complement protein C3 (C3) | X | | X | | X | X |
| Glucagon-like peptide-1 (GLP-1) | X | | X | | | X |
| B cell receptor μ chain (IgM) | X | X | X | | X | X |
| Interleukin-10 (IL-10) | X | | X | | | X |
| Interleukin-11 (IL-11) | X | | X | | X | X |
| Interleukin-13 (IL-13) | X | | X | | | X |
| Interleukin-16 (IL-16) | X | X | X | | X | X |
| Interleukin-18 (IL-18) | X | X | X | | | X |
| Interleukin-1α (IL-1α) | X | X | X | | X | X |
| Interleukin-1ra (IL-1ra) | X | | X | | X | X |
| Interleukin-5 (IL-5) | X | X | X | | | X |
| Interleukin-6 (IL-6) | X | X | X | | | X |
| Interleukin-7 (IL-7) | X | X | X | | X | X |
| Interferon-γ (INF-γ) | X | X | X | | | X |
| Integrin α-11 | X | | X | | | X |
| Janus kinase 3 protein tyrosine kinase (JAK3) | | X | X | | | X |
| Lewis x/CD15 | | X | X | | | X |
| Procathepsin W | X | | X | | | X |
| Properdin | X | X | X | | X | X |
| Sialyl Lewis x | X | | X | | | X |
| C | | | | | | |
| Complement protein C1s (C1s) | | | X | | X | X |
| Eotaxin | | | X | X | X | X |
| Glucagon-like peptide-1 receptor (GLP-1 R) | | | X | | X | X |
| Integrin α-10 | | | X | X | X | X |
| Monocyte chemotactic protein-3 (MCP-3) | | | X | X | X | X |
| D | | | | | | |
| Complement-1 esteras inhibitor (C1-INH) | X | | X | | | |
| Complement protein C5 (C5) | X | X | X | X | | |
| Tumour necrosis factor-α (TNF-α) | X | X | X | X | | |
| E | | | | | | |
| Interleukin-9 (IL-9) | | X | | | | X |
| F | | | | | | |
| Granulocyte-macrophage colony-stimulating factor (GM-CSF) | | | | X | | X |
| Interleukin-2 (IL-2) | | | X | X | | X |
| Leptin | | | X | | | X |
| Lewis y | | | X | | | X |
| Prostate specific antigen (PSA) | | | X | | | X |
| Rantes | | | X | | | X |
| G | | | | | | |
| Angiomotin | X | | | | | |
| Complement protein C4 (C4) | | X | | | | |
| Complement Factor B (Factor B) | X | | | | | |
| H | | | | | | |
| Interleukin-1β (IL-1β) | | | | | | X |
| Monocyte chemotactic protein-4 (MCP-4) | | | | | | X |
| TM peptide | | | | | | X |

TABLE VI

Trained SVM program

The following parameters were obtained using the e1071 1.5-24 SVM, available from http://cran.r-project.org/web/packages/e1071/index.html.
(A) - Definition of a condensed biomarker signature for PaC vs all ( N+Chp +AIP) using a backward elimination strategy

```
filnamn <- "PaC_vs_all_training_set.txt"
group1 <- "other"
group2 <- "PaC"
# Include
source("NaiveBayesian")
library(e1071)
# Hämta data
rawfile <- read.delim(filnamn)
# Läs in grupper
groups <- rawfile[,2]
# Hämta provnamn i datafilen
samplenames <- as.character(rawfile[,1])
# Skapa dataset ur råfilen
data <- t(rawfile[,-c(1,2)])
# Log
# data <- log(data)/log(2)
# antal prover
nsamples <- ncol(data)
# Skapa antikroppsnamnlista ur NYA datafilen
ProteinNames <- read-delim(filnamn,header-FALSE)
ProteinNames <- as.character(as.matrix(ProteinNames) [1,])
ProteinNames <- ProteinNames[-(1:2)]
# Kolla antal Ab i nya datasetet
antal <- length(ProteinNames)
# Ge rätt prov- och Ab-namn
rownames(data) <- ProteinNames
colnames(data) <- samplenames
# Skapa subsets
subset1 <- is.element(groups , strsplit(group1,",")[[1]])
subset2 <- is.element(groups , strsplit(group2,",")[[1]])
# Skapa factorlista
svmfac <- factor(rep('rest',ncol (data
)),levels=c(group1,group2, 'rest'))
svmfac[subset1] <- group1
svmfac[subset2] <- group2
svmfac <- svmfac[subset1|subset2]
#Skapa vektor för K-L felen där det minsta för varje signaturlängd
sparas
smallestErrorPerLength <- rep(NA,antal)
#Beräkna medelvårde för varje Ab over alla prov som är med
averages <- apply(data, 1, mean)
#Skapa vektor for Ab-ordningen efter K-L felen som erhållits när
#respektive antikropp var satt till medelvärde.
abOrder <- rep(NA,antal)
#Skapa ett dataset att eliminera i
elimData <- data[,subset1|subset2]
#Lista att förvara SVM-modellerna i
models <- numeric(nsamples)
#Skapa variabel för att hålla reda på hur många Ab som tagits bort
borttagna <- 0
######################################################################
# BEGIN BACKELIM #####################################################
######################################################################
print(Sys.time( ))
#Kör tills bara två analyter återstår
for (j in 1: (antal-1))
{
    #Check if groups are given in correct order
    control <- as.numeric(svmfac)
    if(sum(control[subset1]) > sum(control[subset2]))
    {
                print ("ERROR: Change order of your group1 and group2!!!")
                break
    }
    # For varje signaturlängd, där alla är med från början, träna en
modell för
    # varje N-1 kombiantion av prover med den data som finns i elimData
    for (i in 1:nsamples)
    {
                # Modellerna sparas i en array av listor kallad models
                models[i] <- list(svm(t(elimData[,-i]), svmfac[-i],
```

TABLE VI-continued

Trained SVM program

```
kernel="linear"))
    }
    # Nu är alla modeller som behövs för LOO tränade och ska testas på
elimData.
    # I elimData sätts först en analyt till medelvärde, sen testas var och
en av
    # modellerna med det prov som var borttaget när den tränades.
    # Nar alla modellerna är testade en gång beräknas KL-fel som sparas i
errors.
    # Nu sätts nasta analyt till medelvärde och testprocessen görs om,
tills alla
    # analyter varit medelvärdeseliminerade en gång. Resultatet blir en
KL-fel
# lista lika lång som antalet analyter som är kvar i datasetet.
    # Skapa en lista med K-L fel en viss signaturlängd (antal + 1 − j
lång)
    # där areorna för varje körning där en Ab i taget har satts till
medelvärde
    errors <- testModels(models, elimData, averages)
    # Lagg namnet på Ab med sämst inverkan på felet i abOrder
    abOrder[j] <- getWorstAb(errors, row.names(elimData))
    # Lägger till värdet på det minsta felet
    smallestErrorPerLength[j] <- getSmallestError(errors)
    # Tar bort sämsta Ab ur medelvärdeslistan
    averages <- getNewAverages(errors, averages)
    # Tar bort sämsta Ab ur elimData
    elimData <- getNewElimData(errors, elimData)
    # Noterar att en Ab tagits bort
    borttagna <- borttagna + 1
    # Ange hur många analyter som eliminerats, samt vad klockan är.
    print(paste(j, "analytes eliminated @", Sys.time( )), sep=" ")
}
# Lägg till namnet på sista analyetn, som aldrig blen eliminerad
abOrder[length(abOrder)] <- setdiff(ProteinNames, abOrder)
# Spara resultatet till fil
filename <- paste("Backward elimination
result(",rnorm(1)+1,").txt",sep=" ")
write.table(cbind(smallestErrorPerLength,abOrder), file=filename,
sep="\t", quote = F,row.names = F)
################################################################
# FUNCTIONS ####################################################
################################################################
# getWorstAb: Rapporterar namnet på antikroppen som kommer tas bort
# (den där ROC-arean var som störst)
getWorstAb <- function(errors, abNames)
{
    return(abNames[order(errors, decreasing = F) [1]])
}
# testModels: testar alla modeller som finns i 'models' med alla
# analyser satta till medelvärde en gång
testModels <- function (models, elimData, averages)
{
    nsamples <- ncol(elimData)
    d <- as.numeric(svmfac)-1
    y <- numeric(nsamples)
    E <- numeric(nsamples)
    analytes <- nrow(elimData)
    errors <- numeric(nrow(elimData))
    for(k in 1:analytes)
    {
                # Sätt analyt k till medelvärde i elimData
                    # Men spara först analytens orginalvarde
                backup <- elimData[k,]
                elimData[k,] <- averages[k]
                # Gör LOO loop för datasetet med de redan färdiga modellena
                for (i in 1:nsamples)
                {
                        pred <- predict(models[[i]] , t(elimData[,i]),
decision.values=TRUE)
                        #spara decision values
                        y[i] <- as.numeric(attributes(pred)$decision.values)
                }
                # Beräkna "sannolikheterna"
                y = 1-(1/(1 − exp(−y)))
                # Beräkna KL-fel när aktuell analyte är eliminerad
```

TABLE VI-continued

Trained SVM program

```
            for (i in 1:nsamples)
            {
                E[i] <- - (d[i] *log(y[i]) + (1-d[i])*log(1-y[i]))
            }
            # Spara felet
            errors[k] <- sum(E)
            # Lägg tillbaka analyten
            elimData[k,] <- backup
        }
        return( errors )
}
# getNewElimData: Väljer vilken antikropp som ska tas bort ur
tränigsdatan och tar bort den
getNewElimData <- function(errors, elimData)
{
    # Positionen for det minsta felet
    tasBort <- order (errors,decreasing = F) [i]
    return(elimData[-tasBort,])
}
# getSmallestError: Rapporterar minsta K-L felet
getSmallestError <- function(errors)
{
    return(min(errors))
}
# getNewAverages: skapar en ny lista med medelvärden efter att en analyt
# eliminerats.
getNewAverages <- function (errors, averages)
{
    # Positionen för det minsta felet
    tasBort <- order(errors, decreasing = F)[1]
    return(averages[-tasBort])
}
# getRemovedAb: tar fram ID på analyt som eliminerats
getRemovedAb <- function (errors, abNames)
{
    return(abNames[order(errors, dedreasing = T) [1]])
}
(B) - Definition of a condensed biomarker signature for PaC vs N using a modified
backward elimination strategy
# Datafil och grupper
                filnamn <- "PaC_vs_N_dataset.txt"
                group1 <- "N"
                group2 <- "PaC"
                # Läs in datafil
                rawfileORG <- read.delim(filnamn)
                # Läs in grupper
                groupsORG <- rawfileORG[,2]
                # Läs in data
                dataORG <- log(t(rawfileORG[,-c(1,2):))
                # Läs in Ab-namn
                ProteinNames <- read.delim(filnamn,header=FALSE)
                ProteinNames <- as.character(as.matrix(ProteinNames)[1,])
                ProteinNames <- ProteinNames[-(1:2)]
                # Kalla Ab rätt namn
                rownames(dataORG) <- ProteinNames
                # Kalla prover rätt namn
                samplenamesORG <- as.character(rawfileORG[,1])
                colnames(dataORG) <- samplenamesORG
                # Kontrollera antalet prover
                NoSamples <- dim(rawfileORG)[1]
                # Kontrollera antalet Ab
                NoAntibodies <- dim(rawfileORG)[2] - 2
                # Skapa subsets utifrån grupepr
                subsetORG1 <- is.element(grcupsORG , strsplit(group1,",")[[1]])
                subsetORG2 <- is.element(groupsORG , strsplit(group2,",")[[1]])
                # Skapa faktorer utifrån subsets
                svmfacORG <- factor(rep('rest',ncol(dataORG
                )),levels=c(group1,group2,'rest'))
                svmfacORG[subsetORG1] <- group1
                svmfacORG[subsetORG2] <- group2
                # Skapa vektor och array får ROC-areor respektive Signaturer
                # från varje körning utan A provet
                BestROCsForEachRun <- rep(NA,NoSamples*NoAntibodies)
                dim(BestROCsForEachRun) <- c(NoSamples,NoAntibodies)
                AbRemovalOrderForEachRun <- rep(NA,NoSamples*NoAntibodies)
                dim(AbRemovalOrderForEachRun) <- c(NoSamples,NoAntibodies)
```

TABLE VI-continued

Trained SVM program

```
# For varje prov i datasetet:
for(A in 1:NoSamples) # for (A in NoSamples:1)
{
    # Hämta data från orginal-råfilen for alla prover utom A
    rawfile <-rawfileORG[-A,]
    # Hämta provnamn i NYA datafilen
    samplenames <- as.character(rawfile[,1])
    # Hämta grupper i NYA datafilen
    groups <- rawfile[,2]
    # Skapa dataset ur NYA datasete
    runData <- t(rawfile[,-c(1,2)])
    # Skapa antikroppsnamnlista ur NYA datafilen
    ProteinNames <- read.delim(filnamn,header=FALSE)
    ProteinNames <- as.character(as.matrix(ProteinNames)[1,])
    ProteinNames <- ProteinNames[-(1:2)]
    # Kolla antal Ab i nya datasetet
    antal <- length (ProteinNames)
    # Ge rätt prov- och Ab-namn
    rownames(runData) <- ProteinNames
    colnames(runData) <- samplenames
    # Skapa nya subsets
    subset1 <- is.eiement(groups , strsplit(group1,",")[[1]])
    subset2 <- is.element(groups , strsplit(group2,",")[[1]])
    # Skapa ny factorlista
    svmfac <- factor(rep('rest',ncol(runData
)),levels=c(group1,group2,'rest'))
    svmfac[subset1] <- group1
    svmfac[subset2] <- group2
    # Skapa vektor för ROC-areor där den bästa för varje signaturlängd
sparas
    bestRocPerLength <- rep(NA,antal)
    # Beräkna medelvärde för varje Ab över alla prov som är med
    averages <- apply(runData, 1, mean)
    # Skapa vektor för At-ordningen efter ROC-areorna som erhållits när
    # respektive antikropp var satt till medelvärde.
    abOrder <-rep(NA,antal)
    # Skapa tränings och testset att köra
    trainData <- runData
    testData <- runData
    # Skapa variabel för att hålla reda på hur många Ab som tagits bort
    borttagna <- 0
    # Kör lika många gånger som antalet Ab – 1
    for(j in 1:(antal-1))
    {
                # Skapa en lista med ROC-areor en viss signaturlängd (antal + 1 – j
lång)
                # där areorna för varje körning där en Ab i taget har satts till
medelvärde
                ROClist <- svmForAbList(antal-borttagna, trainData, svmfac,
averages)
                # Lägg Ab med sämst inverkan på ROC-area
                abOrder[j] <- getRemovedAb(ROClist,row.names(trainData))
                # Skapa ny träningsdata där sämsta Ab tas bort
                trainData <- getNewTrainData(ROClist, trainData)
                # Tar bort sämsta Ab ur medelvärdeslistan
                averages <- getNewAverages(ROClist, averages)
                # Noterar att en Ab tagits bort
                borttagna <- borttagna-1
                # Lägger till värdet på den bästa ROC-arean
                bestRocPerLength[j]<-getBestROC(ROClist)
    }
    # Lägg till den bästa arean för aktuell längd i en lista
    BestROCsForEachRun[A,] <- bestRocPerLength
    # Lägg till vilken Ab som togs bort för aktuell längd i en lista
    AbRemovalOrderForEachRun[A,] <- abOrder
    # Skriv vilken körning som genomförts till prompten
    print(paste(j, "in", A, "of", NoSamples,"at",Sys.time( )))
}
```

TABLE VI-continued

Trained SVM program

```
# Include
source("NaiveBayesian")
library(e1071)
# Skapar en listamed ROC-areor for en vända med ett antal antikroppar
# där alla antikroppar satts till medelvärde en gång
svmForAbList <- function(abNumber, trainData, svmfac, averages)
{
    testData <- trainData
    ROClist <- rep(NA,abNumber)
    for (k in 1:abNumber) # Byter en variabel i träningsdata till
medelvärden,
        {               # kör svmloo, byter tillbaka till ordinalvärdena.
                        testData[k,] <- averages[k]
                        #ROClist[k] <- svmLOOvaluesBE(trainData, testData, svmfac)
                        ROClist[k] <- svmLOOvaluesProb(trainData, testData, svmfac)
                        testData[k,] <- trainData[k,]
        }
    return(ROClist)
}
# Rapporterar namnet på antikroppen som kommer tas bort
# (den där ROC-arean var som störst)
getRemovedAb <- function(ROClist, adNames)
{
    return(abNames(order(ROClist, decreasing = T) [1]))
}
{
# Rapporterar storsta ROC-arean
getBestROC <- function(ROCList)
{
    return(max(ROClist))
}
# Väljer vilken antikropp som ska tas bort ur tränigsdatan och tar bort
den
getNewTrainData <- function(ROClist, trainData)
{
    # Positionen för den största ROC-arean
    tasBort <- order(ROClist,decreasing=T)[1]
    return(trainData[-tasBort,])
}
# Väljer vilken antikropp som ska tas bort ur averages
getNewAverages <- function(ROClist, averages)
{
    # Positionen för den största ROC-arean
    tasBort <- order(ROClist,decreasing=T) [1]
    return(averages[-tasBort])
}
svmLOOvaluesBE <- function(trainData, testData, svmfac)
{
    nsamples <- ncol(trainData)
    res <- numeric(nsamples)
    sign <- numeric(nsamples)
    for (i in 1:nsamples)
                {
                svmtrain <- svm(t(trainData[,-i]) , svmfac[-i] , kernel="linear" )
                pred <- predict(svmtrain , t(testData[,1]) , decison.values=TRUE)
                res[i] <- as.numeric(attributes(pred)$decision.values)
                fen <- colnames(attributes(pred)$decision.values)[1]
if(fcn==paste(levels(svmfac)[1],"/",levels(svmfac)[2],sep=" "))(sign[i]<-
1}
if(fcn==paste(levels(svmfac)[2],"/",levels(svmfac)[1],sep=" "))(sign[i]<-
-1}
        }
    res <- sign * res
    ROCdata <- myROC(res,svmfac)
    return(ROCdata[1])
}
# Tränar svm med viss signatur på viss data och testar på ett prov
test1sample <- function(dataORG, svmfacORG, A, signatureAbs)
{
    svmtrain <- svm(t(dataORG[signatureAbs,-A]) , svmfacORG[-A] ,
kernel="linear")
    pred <- predict(svmtrain , t(dataORG[signatureAbs,A]) ,
decision.values=TRUE)
    res <- as.numeric(attributes(pred)$decision.values)
    return(res)
}
```

TABLE VI-continued

Trained SVM program

```
svmLOOvaluesProb <- function(trainData, testData, svmfac)
{
    nsamples <- ncol(trainData)
    #res <- numeric(nsamples)
    #sign <- numeric(nsamples)
    d <- as.numeric(svmfac) −1
    y <- numeric(nsamples)
    E <- numeric(nsamples)
    for (i in 1:nsamples)
    {
                    svmtrain <- svm(t(trainData[,−i]) , svmfac[−i] , kernel="linear")
                    pred <- predict(svmtrain , t(testData[,i]), decision.values=TRUE)
                    y[i] <- as.numeric(attributes(pred)$decision.values)
    }
    y = 1−(1/(1 − exp (−y)))
                    for (i in 1:nsamples)
                    {
                        E[i] <- −(d[i] *log(y[i]) − (1−d[i] ) *log(1−y[i]))
                    }
                    return(1/sum(E))
}
(C) -Test of signature defined in Table 5(A)
apri<-c(
    "    IL-3 (1)         ",
    "    C3 (1)           ",
    "    C5 (1)           ",
    "    IL-7 (2)         ",
    "    IL-4 (3)         ",
    "    CD40 (2)         ",
    "    TGF-b1 (1)       ",
    "    IL-12 (1)        ",
    "    GM-CSF (1)       ",
    "    Properdin        ",
    "    IgM (B)          ",
    "    VEGF (3)         ",
    "    IL-16 (1)        ",
    "    MUC-1 (P3-15)    ",
    "    IL-1a (1)        ",
    "    TNF-b (1)        ",
    "    Integrin a-10    ",
    "    C1 est. inh.     ",
    "    MCP-1 (3)        ",
    "    MCP-3 (2)        ",
    "    IL-2 (3)         ",
    "    Eotaxin (3)      ",
    "    IL-11 (2)        ",
    "    TNF-a (1)        ",
    "    IL-1-ra (3)      ")
library (MASS)
library (gplots)
library (e1071)
source ("C:/Program/R/R-2.8.1/library/NaiveBayesian")
filnamn<-"PaC_all_data.txt"
rawfile <- read.delim(filnamn)
samplenames <- as.character(rawfile[,1])
groups <- rawfile[,2]
data <- t(rawfile[,−c(1,2)])
ProteinNames <- read.delim(filnamn,header=FALSE)
ProteinNames <- as.character(as.matrix(ProteinNames) [1, ])
ProteinNames <- ProteinNames [- (1:2) ]
rownames(data) <- ProteinNames
colnames(data) <- samplenames
group1 <- "other"
group2 <- "PaC"
nTrainingSamples <- 68
nTestSamples <- 35
training <- data[, 1:nTrainingSamples ]
test <- data[, (nTrainingSamples+1) : (nTrainingSamples+nTestSamples) ]
aprioriBoolean <- is.element (rownames (data) , apri)
facTr <- factor (rep ("rest",ncol (training) ) , levels=c (group1, group2,
"rest") )
subset1Tr <- is.element (groups[1:nTrainingSamples] , group1)
subset2Tr <- is.element (groups[1:nTrainingSamples] , group2)
```

TABLE VI-continued

Trained SVM program

```
facTr[subset1Tr] <- group1
facTr[subset2Tr] <- group2
facTe <- factor(rep("rest", ncol(test)) , levels=c(group1, group2,
"rest") )
subset1Te <-
is.element (groups[(nTrainingSamples+1) : (nTrainingSamples+nTestSamples) ]
, strsplit(group1,",") [[1]])
subset2Te <-
is.element (groups[(nTrainingSamples+1) : (nTrainingSamples+nTestSamples) ]
, strsplit(group2,",") [[1]])
facTe [subset1Te] <- group1
facTe [subset2Te] <- group2
svmtrain <- svm (t (training[aprioriBoolean,]) , facTr, kernel=937 linear")
pred <- predict(svmtrain, t(test[aprioriBoolean, ]) , decision.values =
TRUE, probability = T)
res <- as.numeric (attributes(pred)$decision.values, probability = T)
facnames <- colnames (attributes(pred)$decision.values) [1]
ROCdata <- myROC (res, facTe)
ROCdata[1]
SenSpe <- SensitivitySpecificity(res,facTe)
Sensitivity <- as.numeric(SenSpe[,1])
Specificity <- as.numeric(SenSpe[,2])
omSpecificity <- 1-Specificity
plot(omSpecificity, Sensitivity, ylab="Sensitivity", xlab="1-
Specificity", type="1")
mtext (side=1, line = −1.1, paste("ROC AUC = ",signif(ROCdata[1],
digits=2)))
(D) - Final SVM model for PaC vs all (N+ChP+AIP)
$call
svm.default(x = t(training[aprioriBoolean, ]), y = facTr, kernel = "linear")
$type
[1] 0
$kernel
[1] 0
$cost
[1] 1
$degree
[1] 3
$gamma
[1] 0.04
$coef0
[1] 0
$nu
[1] 0.5
$epsilon
[1] 0.1
$sparse
[1] FALSE
$scaled
[1] TRUE TRUE TRUE TRUE TRUE TRUE TRUE TRUE TRUE TRUE TRUE TRUE TRUE
TRUE TRUE TRUE TRUE TRUE TRUE TRUE TRUE TRUE TRUE TRUE TRUE
$x.scale
$x.scale$'scaled:center'
  C1.est..inh.    C3..1.    C5..1.    CD40..2.    Eotaxin..3.    GM.CSF..1.    IgM..B.    IL.11..2.
  IL.12..1.    IL.16..1.
     24090.45    569451.81    102936.57    22951.29    26674.95    24125.44    20855.98
  14129.86    44608.14    20611.42
       IL.1a..1.    IL.1.ra..3.    IL.2..3.    IL.3..1.    IL.4..3.    IL.7..2.    Integrin.a.10    MCP.1..3.
  MCP.3..2.    MUC.1..P3.15.
     219572.74    19584.88    40985.94    49070.16    24741.71    20879.60    13058.64
  11227.79    14915.23    50846.38
       Properdin    TGF.b1..1.    TNF.a..1.    TNF.b..1.    VEGF..3.
     128296.18    22788.14    13682.89    25428.40    41955.64
$x.scale$'scaled:scale'
  C1.est..inh.    C3..1.    C5..1.    CD40..2.    Eotaxin..3.    GM.CSF..1.    IgM..B.    IL.11..2.
  IL.12..1.    IL.16..1.
     20404.868    122237.943    28461.795    12025.068    13215.275    16954.639
        14666.366
  10156.372    57988.003    13187.529
       IL.1a..1.    ILA.1.ra..3.    IL.2..3.    IL.3..1.    IL.4..3.    IL.7..2.    Integrin.a.10
        MCP.1..3.
  MCP.3..2.    MUC.1..P3.15.
     153112.225    11314.711    76593.575    21019.692    10105.650    19923.025    8856.321
```

TABLE VI-continued

Trained SVM program

```
5452.479    6368.842    28650.095
     Properdin   TGF.b1..1.  TNF.a..1.   TNF.b..1.   VEGF..3.
     56720.049   11069.444   8292.061    12180.614   20857.971
$y.scale
NULL
$nclasses
[i] 2
$levels
[1] "other"  "PaC"  "rest"
$tot.nSV
[1] 27
$nSV
[1] 17 10
$labels
[1] 1 2
$SV
     C1.est..inh.  C3..1.  C5..1.  CD40..2.  Eotaxin..3.  GM.CSF..1.  IgM..B.
     IL.11..2.
IL.12..1.  IL.16..1.  IL.1a..1.
Pa009 −0.75869601 −0.43683015 −0.20743017 −0.005289015 −0.38931564 0.095770897
−0.93670642 −0.05169534 −0.30674506 −0.074417127 0.50792542
Pa038 −0.42410595 −0.73311709 −1.25244853 −0.692015029 −0.05078382 −0.003980786
5.67933331 −0.28192859 −0.28602139 −0.214764177 0.06911333
Pa006 −0.73654816 0.24109661 −0.46040093 −1.012551914 −1.15296122 −0.841258482
−0.72678562 −0.78781462 −0.32368921 −0.848293554 −0.69234178
Pa013 −0.21700833 1.86892400 0.58834639 −0.264721795 −0.68552957 −0.153202159
−0.04927657 0.05757379 −0.08137510 1.221751926 1.08098684
Pa024 1.58648919 1.44742521 0.75444772 −0.284927936 −0.69406449 2.493561060
−0.44527793 −0.39055704 0.29383416 −0.455154737 −0.81120268
Pa056 −0.36431725 −0.46909174 −0.50130198 −0.554747166 −0.35106339 −0.494146089
−0.17013264 −0.60888484 −0.20597864 −0.517666268 1.81952423
Pa125 −0.23467729 0.25849084 0.56420454 0.369299406 0.43426269 0.208651188
1.25308235 −0.20834865 0.08202813 −0.357037439 −0.55800518
Pa001 −0.47076992 0.56381381 0.06633327 0.435287817 0.08932416 −0.222587527
−0.47610845 −0.27857151 −0.35763315 −0.269646986 −0.76364068
Pa010 0.05320001 −0,18419292 −0.59262780 0.130515458 0.29607807 0.356063766
−0.15926715 0.20807177 −0.15588319 0.580881124 −1.35854055
Pa021 0.38072938 −0.51120893 −0.08552594 0.833802541 0.12119111 0.162821416
0.27919151 0.38595265 −0.02303639 0.687902307 −0.40739811
Pa029 −0.39903826 1.23107814 0.03028247 −0.646633317 −0.61805906 −0.141471627
−0.55837741 −0.62561111 −0.08591402 −0.544224442 −0.39352990
Pa048 −0.26957423 0.75584809 −0.08955982 −0.255480195 −0.87836464 −0.745964552
−0.45255194 −0.26172904 0.03931362 −0.449749768 −1.32821555
Pa058 6.10905531 −0.04325893 0.08698841 0.870476656 0.53283461 0.979088486
−0.13691383 −0.05059637 −0.09088942 0.270927629 −0.42939318
Pa092 −0.24149853 −0.22137826 −0.86374589 −0.004986871 −0.21952427 −0.118794005
0.17005557 0.18556909 −0.28585022 0.326046954 −0.87098067
Pa106 −0.23439949 −0.29286642 −0.90705556 1.431821157 0.87865697 1.208446338
−0.20106733 0.67417004 −0.14514808 1.186336278 −0.70633875
Pa128 −0.08417237 0.97358160 0.52585704 −0.062347659 −0.02788034 −0.411255681
0.46178541 −0.17013906 −0.12290537 −0.008370042 −0.89794811
Pa142 −0.50958252 −1.08085583 −1.23272636 −0.299928811 0.33070388 −0.396222532
−0.41999851 −0.39335783 −0.26785141 −0.089558380 −0.27466106
Pa015 −0.71635090 0.14276634 −0.74693179 −0.473760238 −1.26913415 −0.964917983
−0.79188785 −0.58820570 −0.41838792 −0.616645822 0.34550134
Pa025 −0.67904289 1.32071592 −0.29298820 −0.497584785 −0.89584008 −0.363827564
−0.60314141 −0.52579460 −0.42216397 −0.400049252 −0.05516486
Pa027 −0.30026876 0.52136967 −0.53568667 −0.092663002 0.38297396 0.085123350
−0.14805742 −0.08863111 −0.32783954 −0.031648097 −0.41278449
Pa045 2,32770652 1.11229339 2.68850620 −0.053703190 −0.83048219 −0.639849777
−0.14176235 −0.17565594 0.52874104 −0.418407376 0.50156594
Pa047 −0.07301964 −0.60084555 −1.391641969 0.347757599 −0.01329602 −0.298201129
0.07255214 0.10285325 −0.08591223 0.019651353 −0.67791456
Pa100 −0.43294548 −0.20545382 −0.28057938 0.237411951 −0.20538311 −0.003113888
0.42568691 −0.47951871 −0.21867907 −0.315650824 −0.68013358
Pa121 −0.05039884 1.52624676 0,54898444 −0.250353390 0.26504091 −0.228812744
−0.10786287 −0.37683608 −0.30183383 −0.169528272 −0.60888710
Pa129 −0.04672091 −1.20455598 −0.72519120 0.144364354 0.39842641 −0.176936684
1.07960964 0.09003457 −0.28256596 0.455159702 −1.07832336
Pa137 −0.81063375 0.39213184 0.40088436 −1.227901001 −1.21269965 −0.956598086
−0.86084278 −0.79973661 7.63985656 −0.907598547 0.72267511
Pa147 −0.13778847 0.76981229 −1.00254399 −0.050061794 0.15942688 −0.300030972
0.29380087 0.02270757 −0.15355286 −0.030274049 0.78409332
     IL.1.ra..3.  IL.2..3.  IL.3..1.  IL.4..3.  IL.7..2.  Integrin.a.10  MCP.1..3.
     MCP.3..2.
MUC.1..P3.15.  Properdin  TGF.b1..1.
Pa009 −0.873764678 −0.411112998 −1.03076857 −0.78714053 −0.5233176752 −1.0569348707
2.27173362 −1.25407017 −1.0252649 0.1360317 −0.2661644
```

TABLE VI-continued

Trained SVM program

Pa038 −0.206056847 0.009708982 −0.60314751 0.44373161 −0.3919296075 0.8585696202
−0.07305799 −0.03616494 0.8055718 1.6515214 −0.1293500
Pa006 −0.961571105 −0.289056355 −0.34582654 −1.06718063 −0.6638369686 −0.7098872057
−1.23264385 −1.31169599 −0.6500758 −1.3448447 −0.9306547
0.234806863 2.175447589 0.01266928 0.54717541 −0.1957777100−0.4801514210
−0.99759860 −0.91896270 0.6498548 −1.1706810 0.4960250
Pa024 −0.305358326 −0.221631817 0.36267874 −0.18586281 −0.2572215174 −0.0456176001
0.08051256 0.56408243 −0.5609039 −1.1089805 −0.2477406
Pa056 0.217707838 −0.154053300 −0.72632423 −0.17209153 −0.0467640708 −0.5423370601
−0.53963593 −0.61602551 0.9101779 −1.0850042−0.7841200
Pa125 0.275035954 −0.224926621 −0.11926723 1.08023147 −0.0206201972 −0.0008422566
1.28473810 0.48915923 0.6111125 −0.3934791 0.1846749
Pa001 −0.091741993 −0.213105078 −0.47534929 −0.76802149 −0.0327458023 −0.4608177008
−0.98212847 −0.23474026 −0.7966689 −0.2220837 −0.4402696
Pa010 −0.464155570 −0.068647798 0.64754337 −0.22005784 −0.0766204082 0.5695475081
−0.13335331 0.53436185 0.3457089 −0,1103537 −0.2059105
Pa021 0.809674963 0.082111154 0.57592395 0.85625877 0.5975398206 0.3056060393
−0.07617649 1.04456867 2.3882107 0.2397382 0.4214540
Pa029 −0.598511728 −0.226930137 −0.44135325 −0.88287360 −0.4211643576 −0.5463940807
−0.73863658 −0.13480309 −1.0338848 1.3801873 −0.9098994
Pa048 −0.540799012 −0.132230617 −0.48802315−0.40421411 −0.3511893489 −0.2933086328
−0.69288196 −0.32862131 −0.5117169 −0.5428015 −0.6331645
Pa058 −0.216266096 −0.263744491 −0.02111594 0.02466775 0.7903127709 −0.4266999225
0.04047197 0.59968815 −0.6309139 0.2644843 0.4347455
Pa092 0.188422574 −0.178937815 0.55239494 −0.03520631 0.0359698815 −0.1928812726
−0.60201879 −0.03639941 0.2006243 −0.6324198 −0.2174438
Pa106 0.134678555 −0.023059591 0.13626501 0.32218390 −0.0635055923 −0.0806119478
0.09892621 0.72394826 −0.4466987 0.3305753 0.8539264
Pa128 0.007572306 −0.139367554 0.21470674 −0.12000217 −0.1506709444 0.2875368605
−0.35548071 0.63819849 −0.4067314 1.0337810 0.1537436
Pa142 −0.266469132 −0.281152595 0.82774995 −0.25295292 −0.3165063500 −0.3388735672
1.71680502 0.49242804 −0.2902914 1.5769876 −0.3204796
Pa015 −0.414827646 −0.335150876 −0.59577082 −0.84721879 −0.6165233284 −0.5728379380
−1.06685693 −1.32707320 −0.8710250 −1.3049299 −0.7987132
Pa025 −0.614322842 −0.351470829 −0.93514922 −1.21928380 −0.5784378396 −0.7578714150
−1.07065042 −0.36768309 −1.0996868 −1.1292653 −0.8399010
Pa027 −0.289995023 −0.234718460 −0.34640819 −0.11023567 0.0001702044 0.0004392925
−0.35285696 −0.23601985 0.5504571 −0.8609139 0.5920421
Pa045 −0.071721708 −0.122541540 1.74977696 0.33065121 −0.3344757232 −0.0134402551
0.14558436 −0.40419305 0.5895674 −0.9058004 −0.2084024
Pa047 0.579454777 −0.023082065 1.00137061 −0.02504929 0.3732057511 0.4029526915
0.28311658 0.20414137 −0.3904702 1.3038092 −0.3220880
Pa1 00 −0.409728805 −0.323942678 0.13563267 −0.32632146 0.2183483192 −0.5858327012
−0.32588781 0.36754365 −0.8761754 1.0424584−0.3768059
Pa121 −0.177281870 −0.189628137 0.04549011 −0.22387032 0.0960551709 −0.1245495609
−0.01148733 0.08500916 −0.2435519−0.4560824 −0.2646761
Pa129 0.211284366 −0.255781747 0.20501384 −0.08248423 0.7175913867 0.0496293721
0.39857908 0.87914844 0.9371010 −0.3958375 0.6287985
Pa137 −0.641370977 −0.393683315 −1.25425888 1.23623466 −0.7024639259 −0.6739023588
−0.83664778 −0.50259826 −1.1584413−1.1886815 −1.1372398
Pa147 0.091538371 −0.178739738 0.06208210 0.04644500 −0.0264655443 0.1878050701
0.50826277 −0.60143916 1.5374629 1.3112835 0.0817073

TNF.a..1.   TNF.b..1.   VEGF..3.
Pa009 0.40813630 −0.29072629 0.21376386
Pa038 −0.18826712 0.01047747 −0.29116552
Pa006 −0.66615076 −1.03733849 −0.95344856
Pa013 0.13709356 −0.43789203 −0.39786986
Pa024 0.35985522 −0.69484995 −0.39811383
Pa056 −0.32725609 −0.65537476 −0.81052618
Pa125 0.13099818 0.09666528 0.25745881
Pa001 −0.54730109 −0.26784028 −0.01851188
Pa010 −0.07002966 0.14109466 0.47584857
Pa021 0.35647693 0.84739885 1.41457100
Pa029 −0.70424687 0.01067955 −0.12682955
Pa048 −0.88347271 −0.37892814 0.03951195
Pa058 1.71697123 0.18848291 0.01324853
Pa092 −0.43475610 0.92880031 −0.27996250
Pa106 1.01132754 1.45346413 0.67985051
Pa128 −0.59595956 0.29156722 0.09509325
Pa142 0.12253269 0.41393499 −0.31173738
Pa015 −0.93543929 −0.62606091 −0.82759284
Pa025 −0.16053458 −0.51839963 −0.21614866
Pa027 0.20233072 0.41248908 −0.18909465
Pa045 −0.17202350 −0.50984474 0.77281999
Pa047 −0.29192335 0.22268877 0.33534050
Pa100 0.48915718 −0.30606315 −0.21250898
Pa121 −0.45976438 0.09615171 0.28373940
Pa129 0.29426203 0.62249829 0.08120801

TABLE VI-continued

Trained SVM program

Pa137 −0.91532270 −0.81985007 −1.12040867
Pa147 0.11963137 0.13800477 0.29478773
$index
 [1] 1 3 15 16 17 21 24 26 28 30 31 32 34 37 38 42 44 47 48 50 53 54 61 64 66 67 68
$rho
[1] −0.6668827
$compprob
[1] FALSE
$probA
NULL
$probB
NULL
$sigma
NULL
$coefs
       [,1]
 [1,] 0.30343126
 [2,] 0.09542226
 [3,] 1.00000000
 [4,] 0.20660644
 [5,] 0.05461905
 [6,] 0.82341233
 [7,] 0.50601183
 [8,] 1.00000000
 [9,] 0.24168457
[10,] 0.33709008
[11,] 0.15704187
[12,] 0.50405791
[13,] 0.24715788
[14,] 0.85521666
[15,] 0.20152940
[16,] 1.00000000
[17,] 0.50180868
[18,] −1.00000000
[19,] −1.00000000
[20,] −1.00000000
[21,] −0.49831606
[22,] −1.00000000
[23,] −1.00000000
[24,] −1.00000000
[25,] −1.00000000
[26,] −0.10618995
[27,] −0.43058420
$na.action
NULL
$fitted
Pa009 Pa012 Pa038 Pa042 Pa055 Pa063 Pa066 Pa069 Pa081 Pa097 Pa105 Pa108 Pa114
Pa135 Pa006 Pa013 Pa024 Pa033 Pa039 Pa052 Pa056 Pa089 Pa096 Pa125 Pa138
other other other other other other other other other other other other other other other
other
other other other other other other other other
Pa001 Pa007 Pa010 Pa014 Pa021 Pa029 Pa048 Pa053 Pa058 Pa088 Pa091 Pa092 Pa106
Pa110 Pa119 Pa126 Pa128 Pa133 Pa142 Pa145 Pa005 Pa015 Pa025 Pa026 Pa027
other other other other other other other other other other other other other other
other
other other other PaC other PaC PaC PaC
Pa034 Pa040 Pa045 Pa047 Pa070 Pa071 Pa079 Pa080 Pa085 Pa094 Pa100 Pa102 Pa113
Pa121 Pa123 Pa129 Pa137 Pa147
    PaC PaC PaC PaC PaC PaC PaC PaC PaC PaC other PaC PaC PaC PaC
other PaC PaC
Levels: other PaC rest

TABLE VII

ROC-AUC values for differentiation between (A) pancreatic cancer, and (B) normal, chronic pancreatitis, and/or acute inflammatory pancreatitis

| ROC-AUC | Biomarker signature |
|---|---|
| 0.71 | IL-7 |
| 0.69 | Integrin α-10 |
| 0.76 | IL-7 + Integrin α-10 + 1 Table IV B marker |
| 0.79 | IL-7 + Integrin α-10 + 2 Table IV B markers |
| 0.80 | IL-7 + Integrin α-10 + 3 Table IV B markers |
| 0.79 | IL-7 + Integrin α-10 + 4 Table IV B markers |
| 0.81 | IL-7 + Integrin α-10 + 5 Table IV B markers |
| 0.81 | IL-7 + Integrin α-10 + 6 Table IV B markers |
| 0.80 | IL-7 + Integrin α-10 + 7 Table IV B markers |
| 0.84 | IL-7 + Integrin α-10 + 8 Table IV B markers |
| 0.79 | IL-7 + Integrin α-10 + 9 Table IV B markers |
| 0.80 | IL-7 + Integrin α-10 + 10 Table IV B markers |

TABLE VII-continued

ROC-AUC values for differentiation between (A) pancreatic cancer, and (B) normal, chronic pancreatitis, and/or acute inflammatory pancreatitis

| ROC-AUC | Biomarker signature |
|---|---|
| 0.79 | IL-7 + Integrin α-10 + 11 Table IV B markers |
| 0.76 | IL-7 + Integrin α-10 + 12 Table IV B markers |

The core markers +8 preferred markers gave the best ROC-AUC value.

The signature corresponds to (core marked in red):

*IL-7*+Integrin α-10+*BTK*+C1*q*+*IgM*+*IL-9*+Procathepsin *W*+properdin+*TM* peptide+*b*-galactosidase However, all marker combinations had substantial predictive power.

The invention claimed is:

1. An array for determining the presence of pancreatic cancer in an individual,
wherein the array comprises antibodies or antigen-binding fragments thereof that bind to each of the biomarkers listed in Table IV(A) and Table IV(B).

2. A kit for determining the presence of pancreatic cancer comprising:

A) antibodies or antigen-binding fragments thereof that bind to each of the biomarkers listed in Table IV(A) and Table IV(B) or an array comprising said antibodies or antigen-binding fragments thereof; and B) instructions for performing a method for determining the presence of pancreatic cancer in an individual.

* * * * *